(12) United States Patent
Liebeskind et al.

(10) Patent No.: US 8,921,599 B2
(45) Date of Patent: Dec. 30, 2014

(54) PROCESSES FOR FORMING AMIDE BONDS AND COMPOSITIONS RELATED THERETO

(75) Inventors: Lanny S. Liebeskind, Atlanta, GA (US); Wenting Wu, Decatur, GA (US); Zhihui Zhang, Downers Grove, IL (US); Hao Li, Decatur, GA (US); Angus A. Lamar, Atlanta, GA (US)

(73) Assignee: Emory University, Atlanta, GA (US)

( * ) Notice: Subject to any disclaimer, the term of this patent is extended or adjusted under 35 U.S.C. 154(b) by 200 days.

(21) Appl. No.: 13/280,991

(22) Filed: Oct. 25, 2011

(65) Prior Publication Data

US 2012/0107902 A1 May 3, 2012

Related U.S. Application Data

(60) Provisional application No. 61/407,089, filed on Oct. 27, 2010.

(51) Int. Cl.

| C07C 211/08 | (2006.01) |
|---|---|
| C07H 1/00 | (2006.01) |
| C07D 213/82 | (2006.01) |
| C07D 233/90 | (2006.01) |
| C07D 295/192 | (2006.01) |
| C07D 307/52 | (2006.01) |
| C07F 7/18 | (2006.01) |
| C07H 21/02 | (2006.01) |
| C07K 1/00 | (2006.01) |
| C07K 1/02 | (2006.01) |
| C07K 5/062 | (2006.01) |
| C07K 5/065 | (2006.01) |
| C07K 5/068 | (2006.01) |
| C07K 5/072 | (2006.01) |
| C07K 5/087 | (2006.01) |

(52) U.S. Cl.
CPC ............... *C07H 1/00* (2013.01); *C07D 213/82* (2013.01); *C07D 233/90* (2013.01); *C07D 295/192* (2013.01); *C07D 307/52* (2013.01); *C07F 7/1852* (2013.01); *C07F 7/1856* (2013.01); *C07H 21/02* (2013.01); *C07K 1/003* (2013.01); *C07K 1/02* (2013.01); *C07K 5/06026* (2013.01); *C07K 5/06034* (2013.01); *C07K 5/0606* (2013.01); *C07K 5/06078* (2013.01); *C07K 5/06086* (2013.01); *C07K 5/06104* (2013.01); *C07K 5/0812* (2013.01)
USPC .......................... 564/317; 564/316; 556/457

(58) Field of Classification Search
USPC ................... 564/316, 317; 556/457
See application file for complete search history.

(56) References Cited

U.S. PATENT DOCUMENTS

| 6,287,806 B1 | 9/2001 | Nishimura et al. |
| 7,718,598 B1 | 5/2010 | Smythe |
| 2005/0176091 A1 | 8/2005 | Yamada |
| 2011/0077325 A1* | 3/2011 | Luo ............................. 523/152 |

FOREIGN PATENT DOCUMENTS

| WO | 0018789 A1 | 4/2000 |
| WO | 2008059003 A1 | 5/2008 |

OTHER PUBLICATIONS

Horton et al., Synthesis of 3'-C-substituted thymidine derivatives by free-radical techniques: scope and limitations. Carbohydr Res, Feb. 5, 2007;342(2):259-67.
Funatomi et al., Pentafluorophenylammonium triflate (PFPAT): an efficient, practical, and cost-effective catalyst for esterification, thioesterification, transesterification, and macrolactone formation, Green Chem. 2006, 8, 1022.
Ishihara, Dehydrative condensation catalyses, Tetrahedron, 2009, 65, 1085.
Sakakura et al., Widely Useful DMAP-Catalyzed Esterification under Auxiliary Base- and Solvent-Free Conditions, JACS 2007 129, 14775.
Kuckmann et al., Silylchalcogenolates MESiRtBu2 (M = Na, Cu, Zn, Fe; E = S, Se, Te; R = tBu, Ph) and Disilyldichalcogenides tBu2RSiE-ESiRtBu2 (E = S, Se, Te; R = tBu, Ph): Synthesis, Properties, and Structures Inorganic Chemistry, 2005. 44(10): p. 3449-3458.
Gareau et al., Preparation and reactivity studies of 1,2-bis-triisopropylsilanylsulfanyl-alkenes Tetrahedron, 2001. 57(27): p. 5739-5750.
Wojnowski et al., The Reactions of Sodium Silanethiolates with Benzoyl Chloride. The Crystal Structures of (O-silyl) thiobenzoates (tBuO)3SiOC(S)Ph, Ph3SiOC(S)Ph, (2,6-XyO)3SiOC(S)Ph, and of PhC(O)SSSC(O)Ph. Z Anorg Allg Chem. 2008;634:730-734.
Martel et al., 1966, Comptes Rendus des Seances de l'Academie des Sciences, Series C: Sciences Chimques, 263:74-76.
Kato et al., 1973, Bull Chem Soc Jpn., 46: 244-248.
Kricheldor et al., Über synthese and reaktionen mono-und difunktioneller thiocarbonsäure-trimethylsilylester (Syntheses and reactions of mono- and bifunctional thiocarboxylic acid trimethylsilyl esters)1972, Makromolekulare Chemie, 158:223-239.
Ishii and Nakayama, 2005, Thio-, Seleno-, and Telluroacyloxy Functions, R1C(S)OR2, R1C(Se)0R2, R1C(Te) OR2, etc., Comprehensive Organic Functional Group Transformations I, vol. 5, 459-491.
Houben et al vol. 22: Three Carbon—Heteroatom Bonds: Thio-, Seleno- and Tellurocarboxylic Acids and Derivatives, 2005, Science of Synthesis, Glass pp. 85-108.
Anderson, Racemization by the Dicyclohexylcarbodiimide Method of Peptide Synthesis, 1959, JACS, 1958. 80(11):p. 2902-2903.
Fujiwara and Kambe, Thio-, Seleno-, and Telluro-Carboxylic Acid Esters, in Calcogenocarboxylic acid Derivatives, S. Kato, Editor. 2005, Springer Berlin/Heidelberg p. 87-140.

* cited by examiner

*Primary Examiner* — Sudhakar Katakam
*Assistant Examiner* — Pancham Bakshi
(74) *Attorney, Agent, or Firm* — Emory Patent Group

(57) ABSTRACT

The disclosure relates to methods for producing amide bonds and reagents related thereto. In some embodiments, the disclosure relates to methods of producing an amide comprising mixing an O-silylated thionoester and an amine under conditions such that an amide is formed. In another embodiment, the disclosure relates to mixing a thiolacid, a silylating agent, and an amine under conditions such that an amide is formed.

7 Claims, 9 Drawing Sheets

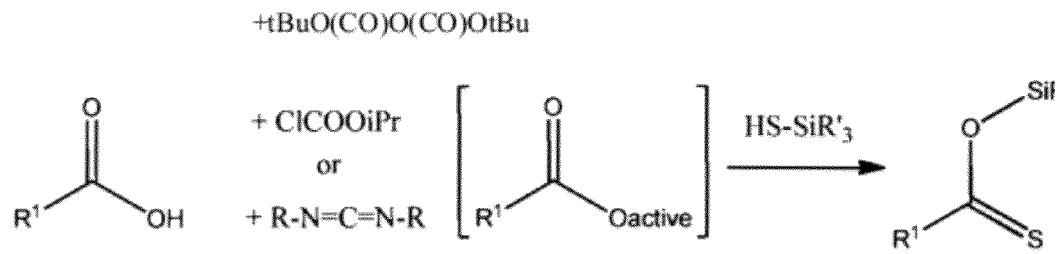
From carboxylic acids plus disulfide or equivalent and a phosphine
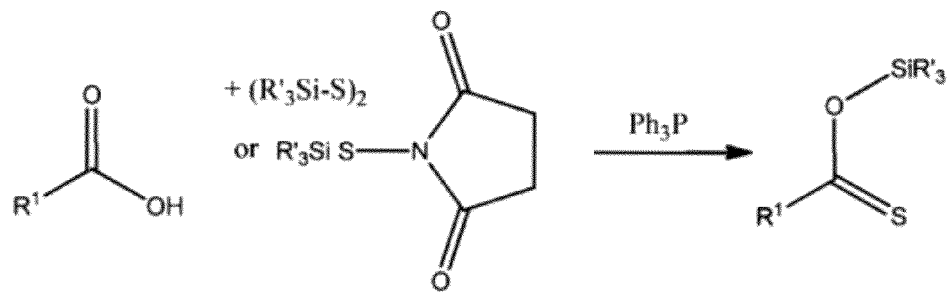
By thiol ester exchange
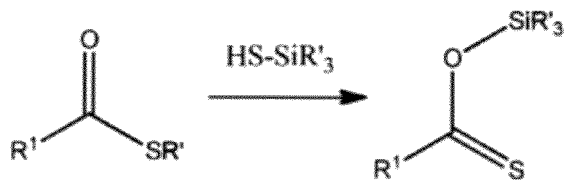
By silylation of thiol acids
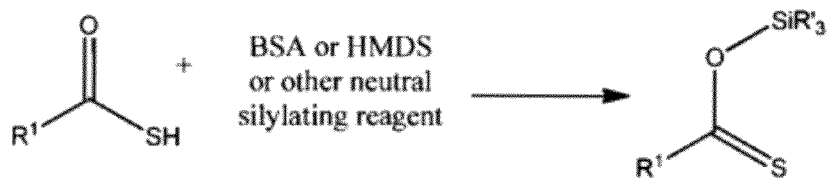
FIG. 3

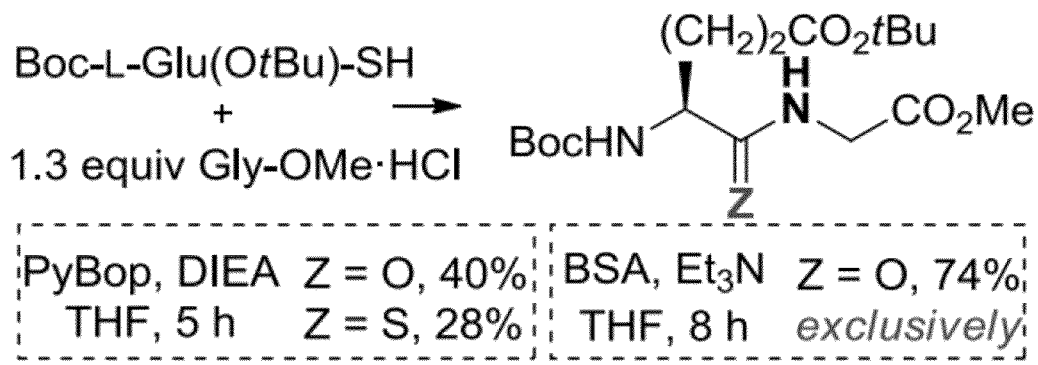

FIG. 4

| entry | amino thiol acid | amino ester | di or tripeptide | time (hr) | yld[a] (%) | epimerization |
|---|---|---|---|---|---|---|
| 1 | Cbz-Gly-SH | L-Phe-OMe·HCl | Cbz-Gly-L-Phe-OMe | 10 10 | 78 71[b] | L/D = 100 : 0 |
| 2 | Cbz-Gly-SH | L-Tyr-OMe·HCl | Cbz-Gly-L-Tyr-OMe | 10 | 69 | |
| 3 | Boc-L-Met-SH | L-Val-OEt·HCl | Boc-L-Met-L-Val-OEt | 10 | 83 | LL/DL > 99 : 1 |
| 4 | Boc-L-Phe-SH | L-Ala-OEt·HCl | Boc-L-Phe-L-Ala-OEt | 12 | 72 | LL/DL > 99 : 1 |
| 5 | Boc-L-Glu(OtBu)-SH | L-Val-OMe·HCl | Boc-L-Glu(OtBu)-L-Val-OMe | 10 | 71 | LL/DL > 99 : 1 |
| 6 | Boc-L-Glu(OBn)-SH | Gly-OEt·HCl | Boc-L-Glu(OBn)-Gly-OEt | 8 | 76 | |
| 7 | Boc-L-Glu(OBn)-SH | L-Met-OMe·HCl | Boc-L-Glu(OBn)-L-Met-OMe | 10 | 68 | |
| 8 | Boc-L-Glu(OBn)-SH | L-Trp-OMe·HCl | Boc-L-Glu(OBn)-L-Trp-OMe | 8 | 74 | |
| 9 | Boc-L-Pro-SH | L-Val-OMe·HCl | Boc-L-Pro-L-Val-OMe | 10 | 65 | |
| 10 | Boc-L-Val-SH | L-Pro-OMe·HCl | Boc-L-Val-L-Pro-OMe | 48 | 70 | |
| 11 | Boc-L-Val-SH | L-Phe-OMe·HCl | Boc-L-Val-L-Phe-OMe | 63 | 67 | |
| 12 | Boc-Aib-SH | L-Trp-OMe·HCl | Boc-Aib-L-Trp-OMe | 54 | 74 | |
| 13 | Boc-L-Phe-L-Pro-SH | L-Ala-OEt·HCl | Boc-L-Phe-L-Pro-L-Ala-OEt | 8 | 65[c] | LLL/LDL > 99 : 1 |
| 14 | Cbz-Gly-L-Phe-SH | Gly-OEt·HCl | Cbz-Gly-L-Phe-Gly-OEt | 15 | 80 60[c] 73[d] | L/D > 96 : 4 L/D > 96 : 4 L/D = 97 : 3 |
| 15 | Cbz-Gly-L-Phe-SH | L-Val-OMe·HCl | Cbz-Gly-L-Phe-L-Val-OMe | 15 | 74 50[c] 55[d] | LL/DL > 95 : 5 LL/DL > 96 : 4 LL/DL > 97 : 3 |

FIG. 5

A
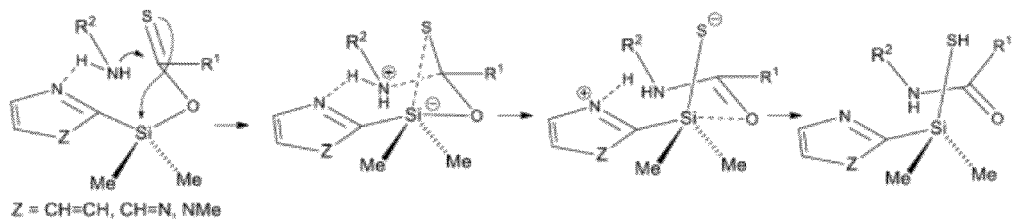
Z = CH=CH, CH=N, NMe
B
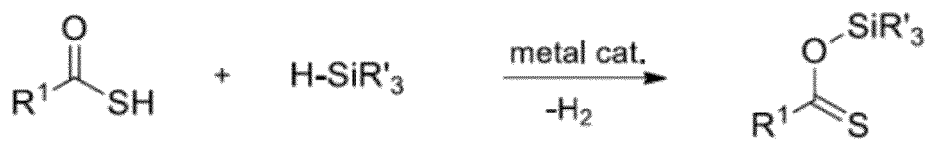
C
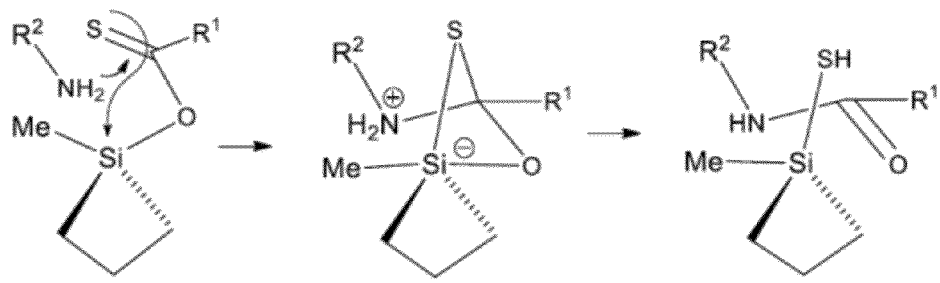
D
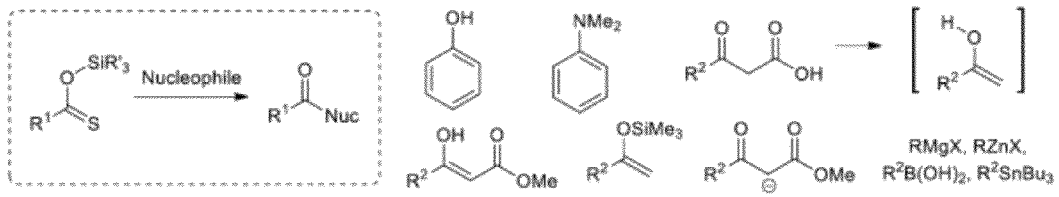
FIG. 6

A
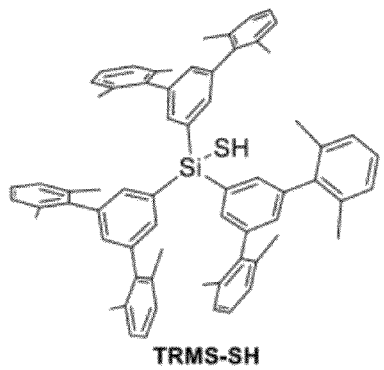
TRMS-SH
B
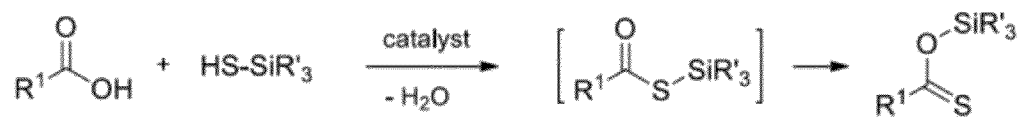
Catalysts: onium Brønsted acid, boronic acids, transition metal Lewis acids, Bi(OTf)$_3$
C
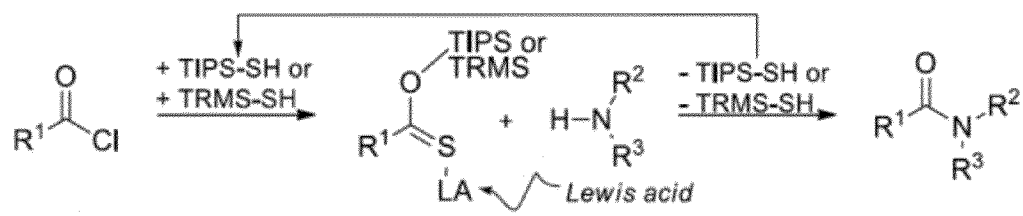
FIG. 7

A
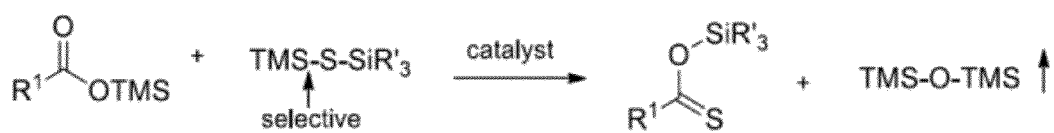
B
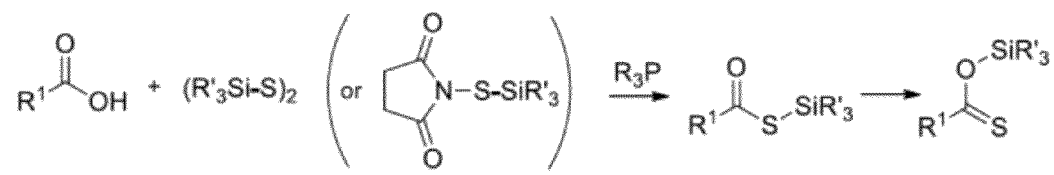
FIG. 8

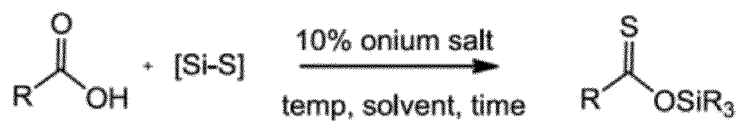

| Entry | [Si-S] | R | catalyst | solvent | temp | time (hrs) | result |
|---|---|---|---|---|---|---|---|
| 1 | TIPSSH | Bn | PFPAT | toluene | 80, reflux | 48 | no rxn |
| 2 | Ph₃SiSH | Bn | PFPAT | toluene | 80, reflux | 48 | no rxn |
| 3 | Ph₂MeSiSH | Bn | PFPAT | toluene | 80, reflux | 48 | (hydrolysis of [Si-S]) |
| 4 | TMS-S-TMS | Bn | PFPAT | toluene | 80, reflux | 48 | (hydrolysis of [Si-S]) |
| 5 | Ph₃SiSH | Bn | PFPAT | xylenes | reflux | 24 | >90% conv. prod |
| 6 | TIPSSH | Bn | PFPAT | xylenes | reflux | 22 | no rxn |
| 7 | Ph₂MeSiSH | Bn | PFPAT | xylenes | reflux | 22 | (hydrolysis of [Si-S]) |
| 8 | Ph₃SiSH | Bn | DPAT | xylenes | reflux | 22 | ~60% conv. prod |

FIG. 10A

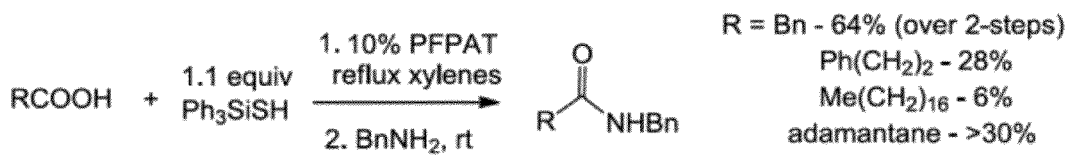

FIG. 10B

PROCESSES FOR FORMING AMIDE BONDS AND COMPOSITIONS RELATED THERETO

CROSS REFERENCE TO RELATED APPLICATIONS

This application claims priority to U.S. Provisional Application Ser. No. 61/407,089, filed Oct. 27, 2010, which applications is hereby incorporated by this reference in its entirety.

ACKNOWLEDGEMENTS

This invention was made with government support under Grants 5RO1GM043107 awarded by the National Institutes of Health. The government has certain rights in the invention.

FIELD

The disclosure relates to methods for producing amide bonds and reagents related thereto. In some embodiments, the disclosure relates to methods of producing an amide comprising mixing an O-silylated thionoester and an amine under conditions such that an amide is formed. In another embodiment, the disclosure relates to mixing a thiolacid, a silylating agent, and an amine under conditions such that an amide is formed.

BACKGROUND

Amide bonds are key component in many biological materials and known drugs. For example, Atorvastatin, which blocks the production of cholesterol, and Valsartan, a blockade of angiotensin-II receptors, both contain amide bonds. Mild, efficient and general methods for the construction of amide and peptide linkages are desired for the production of therapeutics and biological tools that are based upon peptide, protein, and glycopeptides motifs.

Amide bonds are typically synthesized from the union of carboxylic acids and amines; however, the reaction between these two functional groups is not spontaneous at ambient temperature, with the elimination of water only taking place at extremely high temperatures (>200° C.), conditions which are typically detrimental to the integrity of the reacting compounds themselves.

Some coupling methods used to generate amide bonds from carboxylic acids and amines utilize special activating protocols or the construction of special functionalities such as azides and ketoacids or hydroxylamines. There are a number of 'coupling reagents' which convert the —OH of the carboxylic acid to a good leaving group prior to the treatment with the amine. Classical reagents include carbodiimides, phosphonium salts, uronium salts and reagents generating acid halides.

Generating amine reactive acid halides, using reagents such as thionyl chloride and phosphorus pentachloride, is not compatible with many synthetic strategies, due to the formation of hydrochloric acid. Newer reagents used to generate acid halides such as Deoxo-Fluor and DAST are expensive, hazardous, and require purification by chromatography after the reaction.

Carbodiimides such as dicyclohexylcarbodiimide (DCC) are commonly used as coupling reagents; however, these reagents need to be used in conjunction with additives such as 1-hydroxy-1H-benzotriazole (HOBt) or 1-hydroxy-7-azabenzotriazole (HOAt) in order to decrease undesired epimerization that can occur when using chiral amino acids. These additives yield by-products that catalyze the 'dimerization' of DCC. In addition to this, safety considerations have to be carefully considered when using benzotriazoles (or variants thereof) because of their explosive properties.

The coupling reagents based on the HOBt/HOAt system, such as uronium/aminium salts like HATU react with the carboxylic acids to form active esters; however, side reactions of the coupling reagents with the amines lead to the formation of guanidinium side products. The phosphonium salts, which are also based on HOBt/HOAt, such as BOP are undesirable due to the carcinogenic and respiratory toxicity associated with HMPA generated in the reaction.

More recent approaches to amide bond formation include Staudinger ligation, a modification of the Staudinger reaction which produces an amide linked product from the reaction of a modified triarylphosphine and azides, as well as the further modified version which involves the reaction of thioacids with azides. Another method is the 'native chemical ligation' method which is used for the preparation of proteins. It involves the reaction between a peptide alpha-thioester and a cysteine-peptide, to yield a product with a native amide bond at the ligation site. However, the thioalkyl esters are rather unreactive and despite the use of a catalyst the reaction typically takes 24-28 hours.

Although the above methodologies have been applied to the synthesis of proteins and protein analogues, there is a continued interest in the wider application of the tools of organic chemistry to the study of proteins. Despite the number of coupling reagents that have been reported, most reagents are simply not efficient for a broad range of amide bond forming reactions. Thus, there remains a need for simple, effective reagents with high conversions and low levels of epimerization of chiral compounds that produces limited by-products.

Certain catalytic dehydrative condensation reactions are reported by the reaction of carboxylic acids and phosphoric acids with alcohols and amines to give esters and amides. See Funatomi et al., Green Chem. 2006, 8, 1022; Ishihara, Tetrahedron 2009, 65, 1085; and Sakakura et al., JACS 2007, 129, 14775.

SUMMARY

The disclosure relates to methods for forming amide bonds as well as peptide and glycopeptides bonds. In certain embodiments, the disclosure relates to methods of making a compound with an amide bond comprising mixing an O-silylated thionoester and a primary or secondary amine under conditions such that an amide is formed. In certain embodiments, the disclosure relates to methods for amide and peptide construction via S-silylthiol esters generated in situ from carboxylic acids, and/or oxo esters, under mild conditions. In certain embodiments, the reaction is illustrated by Scheme 1.

Scheme 1

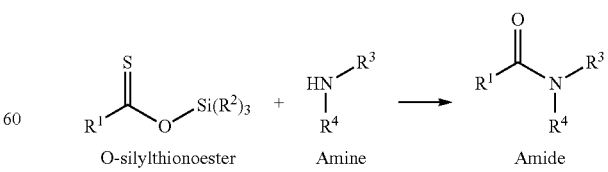

$R^1$ may be chosen from: H, an alkyl group, an alkenyl group, an alkynyl group or a cycloalkyl group, an aryl group, a heterocarbocycyl group, a heteroaromatic group, an acyl group, an alkanoyl group, any of which may be suitably substituted. The O-silylated thionoester may part of an amino acid or a polypeptide wherein the N is suitably protected; the group $R^2$ may be selected from hydrogen, lower alkyl, alkoxy, aromatic, or heteroaromatic groups, wherein $R^2$ may be optionally substituted with one or more substituents such as halogens, alkyl, or alkoxy. In some embodiments the silicon atom of the O-silylthionoester may be linked to a solid phase support. The silylating agent may be a water soluble thiol reagent for applications in water.

$R^3$ and $R^4$ are independently selected from H, an alkyl group, an alkenyl group, an alkynyl group or a cycloalkyl group, an aryl group, a heterocarbocycyl group, a heteroaromatic group, and an acyl group any of which may be suitably substituted. $R^3$ and $R^4$ may be covalently linked to each other. In some embodiments, the amine may be part of an amino acid or a polypeptide chain, or a protein or a glycoprotein or a fully or partially protected derivative thereof. In specific embodiments, the amine may be part of an amino acid where the carboxylic acid functionality is esterified.

In typical embodiments, an N-protected amino acids O-silylthionoester reacts with an amino acid ester to produce a peptide bond as depicted in Scheme 2.

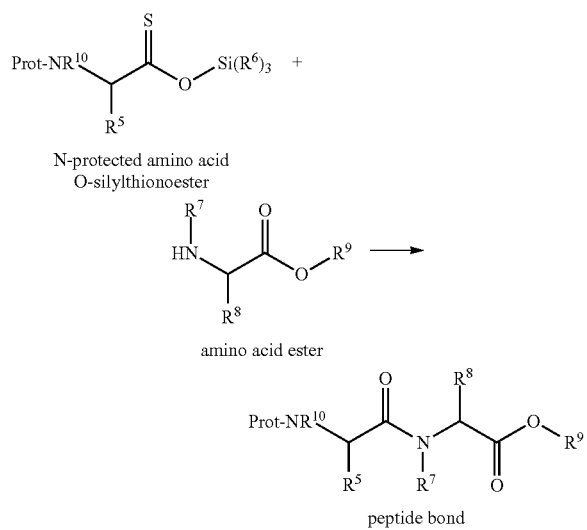

Prot is a protecting group, peptide, or linker to a substrate or biological material;

$R^5$ may be chosen from: H, an alkyl group, an alkenyl group, an alkynyl group or a cycloalkyl group, an aryl group, a heterocarbocycyl group, a heteroaromatic group, an acyl group, an alkanoyl group, any of which may be suitably substituted; the group $R^6$ may be selected from lower alkyl, alkoxy, aromatic, or heteroaromatic groups wherein $R^6$ is optionally substituted by one or more substituents independently selected from halogen, alkyl, and alkoxy;

$R^7$ and $R^8$ are independently selected from H, an alkyl group, an alkenyl group, an alkynyl group or a cycloalkyl group, an aryl group, a heterocarbocycyl group, a heteroaromatic group, an acyl group, an alkanoyl group, any of which may be suitably substituted; $R^7$ and $R^8$ may be covalently linked to each other and the group $R^9$ may be selected from a lower alkyl group;

$R^{10}$ may be hydrogen, alkyl, or acyl or $R^{10}$ and Prot and the attached atoms form a protecting group comprising a 4 to 7 member heterocyclic ring such as a succinimide, maleimide, or phthalimide which may be substituted with one or more substituents, or $R^5$ and $R^{10}$ and the atoms which they are attached may form a 4 to 7 membered heterocyclic ring which may be substituted with one or more substituents.

In some embodiments, the disclosure relates to compounds comprising the following formula:

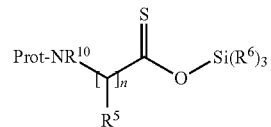

or salts thereof wherein,

Prot is a protecting group, peptide, or linker to a substrate or biological material, or $R^{13}$;

n is 1, 2, 3, 4, 5, or 6;

each $R^5$ is independently selected from hydrogen, alkyl, hydroxyalkyl, thiolalkyl, aminoalkyl, selenoalkyl, carboxylalkyl, aryl, or heterocyclyl, and wherein $R^5$ is optionally substituted by one or more $R^{11}$;

each $R^6$ is independently selected from hydrogen, lower alkyl, alkoxy, aryl, and heterocyclyl, wherein $R^6$ is optionally substituted by one or more substituents independently selected from halogen, alkyl, and alkoxy;

$R^{10}$ is hydrogen, alkyl, acyl, or $R^{10}$ and Prot and the attached atoms form a protecting group comprising a 4 to 7 member heterocyclic ring such as a succinimide, maleimide, or phthalimide which may be substituted with one or more substituents, such as one or more $R^{11}$ or or $R^{10}$ and $R^5$ and the atoms to which they are attached to form a 4-7 membered heterocyclic ring optionally substituted with one or more $R^{11}$;

$R^{11}$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{11}$ is optionally substituted with $R^{12}$;

$R^{12}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl; and $R^{13}$ is alkyl, alkanoyl, formyl, alkylcarboxy, alkylcarbamoyl wherein $R^{13}$ is optionally substituted with one or more $R^{14}$;

$R^{14}$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{14}$ is optionally substituted with one or more $R^{15}$;

$R^{15}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl In certain embodiments, $R^5$ and $R^{10}$ or $R^{10}$ and Prot form a 5 or 6 membered ring.

In certain embodiments, Prot is tert-butoxycarbonyl (Boc) or fluorenylmethyloxycarbonyl (Fmoc).

In certain embodiments, n is 1 or 2.

In certain embodiments, the biological material is a peptide, enzyme, receptor, nucleic acid, cell, antibody, saccharide, polysaccharide, or glycopeptide.

In certain embodiments, the linker is a peptide, a nucleic acid, hydrocarbon, polyethylene glycol, polysaccharide, acrylate polymer, or other polymer.

In some embodiments, the disclosure relates to a compound selected from N-alpha-Boc-alanine-O-trimethylsilylthionoester, N-beta-Boc-beta-alanine-O-trimethylsilylthionoester, N-alpha-Boc-N-alpha-methyl-alanine-O-trimethylsilylthionoester, N-alpha-Boc-alpha-aminobutyric acid O-trimethylsilylthionoester, N-Boc-4-aminobutanoic acid O-trimethylsilylthionoester, N-alpha-Boc-alpha-aminoisobutyric acid O-trimethylsilylthionoester, N-alpha-Boc-$N^G$-(4-Methoxy-2,3,6 trimethylbenzenesulfonyl)-arginine-O trimethylsilylthionoester, N-alpha-Boc-$N^G$-nitro-arginine-O-trimethylsilylthionoester, N-alpha-Boc-$N^G$-tosyl-arginine-O-trimethylsilylthionoester, N-alpha-Boc-$N^G$, $N^G$-bis-CBZ-arginine-O-trimethylsilylthionoester, N-alpha-Boc-asparagine-O-trimethylsilylthionoester, N-alpha-Boc-asparagine-O-trimethylsilylthionoester, N-alpha-Boc-beta-trityl-asparagine-O-trimethylsilylthionoester, N-alpha-Boc-N-beta-xanthyl-asparagine-O-trimethylsilylthionoester, N-alpha-Boc-isoasparagine-O-trimethylsilylthionoester, N-alpha-Boc-aspartic acid alpha-O-trimethylsilylthionoester beta-1-adamantyl ester, N-alpha-Boc-aspartic acid alpha-O-trimethylsilylthionoester beta-2-adamantyl ester, N-alpha-Boc-aspartic acid alpha-benzyl ester beta-O-trimethylsilylthionoester, N-alpha-Boc-N-alpha-methyl-valine-O-trimethylsilylthionoester, N-alpha-Boc-valine-O-trimethylsilylthionoester, N-Boc-6-aminohexanoic acid O-trimethylsilylthionoester, N-alpha-Boc-tert-leucine-O-trimethylsilylthionoester, N-alpha-Boc-S-acetamidomethyl-cysteine-O-trimethylsilylthionoester, N-alpha-Boc-S-benzyl-cysteine-O-trimethylsilylthionoester, N-alpha-Boc-S-p-methylbenzyl-cysteine-O-trimethylsilylthionoester, N-alpha-Boc-S-p-methoxybenzyl-cysteine-O-trimethylsilylthionoester, N-alpha-Boc-S-trityl-cysteine-O-trimethylsilylthionoester, N-alpha-Boc-beta-cyclohexyl-alanine-O-trimethylsilylthionoester, N-alpha-Boc-glutamic acid gama-O-trimethylsilylthionoester alpha-benzyl ester, N-alpha-Boc-glutamic acid gama-benzyl ester alpha-O-trimethylsilylthionoester, N-alpha-Boc-glutamic acid gama-cyclohexyl ester alpha-O-trimethylsilylthionoester, N-alpha-Boc-glutamic acid gama-tert-butyl ester alpha-O-trimethylsilylthionoester, N-alpha-Boc-gama-trityl-glutamine-O-trimethylsilylthionoester, N-alpha-Boc-gama-xanthyl-glutamine-O-trimethylsilylthionoester, N-alpha-N-im-di-Boc-histidine-O-trimethylsilylthionoester, N-alpha-Boc-N-im-tosyl-histidine-O-trimethylsilylthionoester, N-alpha-Boc-N-im-dinitrophenyl-histidine-O-trimethylsilylthionoester, N-alpha-Boc-N-im-trityl-histidine-O-trimethylsilylthionoester, N-alpha-Boc-trans-4-hydroxyproline-O-trimethylsilylthionoester, N-alpha-Boc-glycine-O-trimethylsilylthionoester, N-alpha-Boc-isoleucine-O-trimethylsilylthionoester, N-alpha-Boc-N-epsilon-acetyl-lysine-O-trimethylsilylthionoester, N-alpha,epsilon-di-Boc-lysine-O-trimethylsilylthionoester, N-alpha-Boc-N-epsilon-2-chloro-CBZ-lysine-O-trimethylsilylthionoester, N-alpha-Boc-N-epsilon-trifluoroacetyl-lysine-O-trimethylsilylthionoester, N-alpha-Boc-leucine-O-trimethylsilylthionoester, N-alpha-Boc-methionine-sulfone-O-trimethylsilylthionoester, N-alpha-Boc-methionine-O-trimethylsilylthionoester, N-alpha-Boc-methionine-sulfoxide-O-trimethylsilylthionoester, N-alpha-Boc-N-alpha-methyl-norleucine-O-trimethylsilylthionoester, N-alpha-Boc-norleucine-O-trimethylsilylthionoester, N-alpha-Boc-norvaline-O-trimethylsilylthionoester, N-alpha-Boc-3,4-dehydro-proline-O-trimethylsilylthionoester, N-alpha-Boc-proline-O-trimethylsilylthionoester, N-alpha-Boc-N-alpha-methyl-phenylalanine-O-trimethylsilylthionoester, N-alpha-Boc-4-chloro-phenylalanine-O-trimethylsilylthionoester, N-alpha-Boc-phenylalanine-O-trimethylsilylthionoester, N-alpha-Boc-phenylglycine-O-trimethylsilylthionoester, N-alpha-Boc-N-δ-benzyloxycarbonyl-ornithine-O-trimethylsilylthionoester, N-alpha-Boc-sarcosine-O-trimethylsilylthionoester, N-alpha-Boc-O-benzyl-serine-O-trimethylsilylthionoester, N-alpha-Boc-O-methyl-serine-O-trimethylsilylthionoester, N-alpha-Boc-O-tert-butyl-serine-O-trimethylsilylthionoester, N-1-Boc-1,2,3,4,-tetrahydro-isoquinoline-3-carboxylic acid alpha-O-trimethylsilylthionoester, N-alpha-Boc-N-in-Boc-trypophan-O-trimethylsilylthionoester, N-alpha-Boc-N-in-formyl-tryptophan-O-trimethylsilylthionoester, N-alpha-Boc-N-in-mesitylene-2-sulfonyl-tryptophan-O-trimethylsilylthionoester, N-alpha-Boc-tyrosine-O-trimethylsilylthionoester, N-alpha-Boc-N-alpha-methyl-O-benzyl-tyrosine-O-trimethylsilylthionoester, N-alpha-Boc-O-2-bromobenzyloxycarbonyl-tyrosine-O-trimethylsilylthionoester, N-alpha-Boc-O-benzyl-tyrosine-O-trimethylsilylthionoester, N-alpha-Boc-O-2,6-dichlorobenzyl-tyrosine-O-trimethylsilylthionoester, N-alpha-Boc-O-ethyl-tyrosine-O-trimethylsilylthionoester, N-alpha-Boc-O-methyl-tyrosine-O-trimethylsilylthionoester, N-alpha-Boc-O-tert-butyl-tyrosine-O-trimethylsilylthionoester, N-alpha-Boc-O-benzyl-threonine-O-trimethylsilylthionoester, and N-alpha-Boc-threonine-O-trimethylsilylthionoester, N-alpha-Fmoc-alanine-O-trimethylsilylthionoester, N-beta-Fmoc-beta-alanine-O-trimethylsilylthionoester, N-alpha-Fmoc-N-alpha-methyl-alanine-O-trimethylsilylthionoester, N-alpha-Fmoc-alpha-aminobutyric acid O-trimethylsilylthionoester, N-Fmoc-4-aminobutanoic acid O-trimethylsilylthionoester, N-alpha-Fmoc-alpha-aminoisobutyric acid O-trimethylsilylthionoester, N-alpha-Fmoc-$N^G$-(4-Methoxy-2,3,6 trimethylbenzenesulfonyl)-arginine-O-trimethylsilylthionoester, N-alpha-Fmoc-$N^G$-nitro-arginine-O-trimethylsilylthionoester, N-alpha-Fmoc-$N^G$-tosyl-arginine-O-trimethylsilylthionoester, N-alpha-Fmoc-$N^G$, $N^G$-bis-CBZ-arginine-O-trimethylsilylthionoester, N-alpha-Fmoc-asparagine-O-trimethylsilylthionoester, N-alpha-Fmoc-asparagine-O-trimethylsilylthionoester, N-alpha-Fmoc-beta-trityl-asparagine-O-trimethylsilylthionoester, N-alpha-Fmoc-N-beta-xanthyl-asparagine-O-trimethylsilylthionoester, N-alpha-Fmoc-isoasparagine-O-trimethylsilylthionoester, N-alpha-Fmoc-aspartic acid alpha-O-trimethylsilylthionoester beta-1-adamantyl ester, N-alpha-Fmoc-aspartic acid alpha-O-trimethylsilylthionoester beta-2-adamantyl ester, N-alpha-Fmoc-aspartic acid alpha-benzyl ester beta-O-trimethylsilylthionoester, N-alpha-Fmoc-N-alpha-methyl-valine-O-trimethylsilylthionoester, N-alpha-Fmoc-valine-O-trimethylsilylthionoester, Fmoc-6-aminohexanoic acid O-trimethylsilylthionoester, N-alpha-Fmoc-tert-leucine-O-trimethylsilylthionoester, N-alpha-Fmoc-S-acetamidomethyl-cysteine-O-trimethylsilylthionoester, N-alpha-Fmoc-S-benzyl-cysteine-O-trimethylsilylthionoester, N-alpha-Fmoc-S-p-methylbenzyl-cysteine-O-trimethylsilylthionoester, N-alpha-Fmoc-S-p-methoxybenzyl-cysteine-O-trimethylsilylthionoester, N-alpha-Fmoc-S-trityl-cysteine-O-trimethylsilylthionoester, N-alpha-Fmoc-beta-cyclohexyl-alanine-O-trimethylsilylthionoester, N-alpha-Fmoc-glutamic acid gama-O-trimethylsilylthionoester alpha-benzyl ester, N-alpha-Fmoc-glutamic acid gama-benzyl ester alpha-O-trimethylsilylthionoester, N-alpha-Fmoc-glutamic acid gama-cyclohexyl ester alpha-O-trimethylsilylthionoester, N-alpha-Fmoc-glutamic acid gama-tert-butyl ester alpha-O-trimethylsilylthionoester, N-alpha-Fmoc-gama-trityl-glutamine-O-trimethylsilylthionoester, N-alpha-Fmoc-gama-xanthyl-glutamine-O-trimethylsilylthionoester, N-alpha-N-im-di-Fmoc-histidine-O-trimethylsilylthionoester, N-alpha-Fmoc-N-im-tosyl-histidine-O-trimethylsilylthionoester, N-alpha-Fmoc-N-im-dinitrophenyl-histidine-O-trimethylsilylthionoester, N-alpha-Fmoc-N-im-trityl-histidine-O-trimethylsilylthionoester, N-alpha-Fmoc-trans-4-hydroxyproline-O-trimethylsilylthionoester, N-alpha-Fmoc-glycine-O-trimethylsilylthionoester, N-alpha-Fmoc-isoleucine-O-trimethylsilylthionoester, N-alpha-Fmoc-N-epsilon-acetyl-lysine-O-trimethylsilylthionoester, N-alpha,epsilon-di-Fmoc-lysine-O-trimethylsilylthionoester, N-alpha-Fmoc-N-epsilon-2-chloro-CBZ-lysine-O-trimethylsilylthionoester, N-alpha-Fmoc-N-epsilon-trifluoroacetyl-lysine-O-trimethylsilylthionoester, N-alpha-Fmoc-leucine-O-trimethylsilylthionoester, N-alpha-Fmoc-methionine-sulfone-O-trimethylsilylthionoester, N-alpha-Fmoc-methionine-O-trimethylsilylthionoester, N-alpha-Fmoc-methionine-sulfoxide-O-trimethylsilylthionoester, N-alpha-Fmoc-N-alpha-methyl-norleucine-O-trimethylsilylthionoester, N-alpha-Fmoc-norleucine-O-trimethylsilylthionoester, N-alpha-Fmoc-norvaline-O-trimethylsilylthionoester, N-alpha-Fmoc-3,4-dehydro-proline-O-trimethylsilylthionoester, N-alpha-Fmoc-proline-O-trimethylsilylthionoester, N-alpha-Fmoc-N-alpha-methyl-phenylalanine-O-trimethylsilylthionoester, N-alpha-Fmoc-4-chloro-phenylalanine-O-trimethylsilylthionoester, N-alpha-Fmoc-phenylalanine-O-trimethylsilylthionoester, N-alpha-Fmoc-phenylglycine-O-trimethylsilylthionoester, N-alpha-Fmoc-N-δ-benzyloxycarbonyl-ornithine-O-trimethylsilylthionoester, N-alpha-Fmoc-sarcosine-O-trimethylsilylthionoester, N-alpha-Fmoc-O-benzyl-serine-O-trimethylsilylthionoester, N-alpha-Fmoc-O-methyl-serine-O-trimethylsilylthionoester, N-alpha-Fmoc-O-tert-butyl-serine-O-trimethylsilylthionoester, N-1-Fmoc-1,2,3,4,-tetrahydro-isoquinoline-3-carboxylic acid alpha-O-trimethylsilylthionoester, N-alpha-Fmoc-N-in-Fmoc-trypophan-O-trimethylsilylthionoester, N-alpha-Fmoc-N-in-formyl-tryptophan-O-trimethylsilylthionoester, N-alpha-Fmoc-N-in-mesitylene-2-sulfonyl-tryptophan-O-trimethylsilylthionoester, N-alpha-Fmoc-tyrosine-O-trimethylsilylthionoester, N-alpha-Fmoc-N-alpha-methyl-O-benzyl-tyrosine-O-trimethylsilylthionoester, N-alpha-Fmoc-O-2-bromobenzyloxycarbonyl-tyrosine-O-trimethylsilylthionoester, N-alpha-Fmoc-O-benzyl-tyrosine-O-trimethylsilylthionoester, N-alpha-Fmoc-O-2,6-dichlorobenzyl-tyrosine-O-trimethylsilylthionoester, N-alpha-Fmoc-O-ethyl-tyrosine-O-trimethylsilylthionoester, N-alpha-Fmoc-O-methyl-tyrosine-O-trimethylsilylthionoester, N-alpha-Fmoc-O-tert-butyl-tyrosine-O-trimethylsilylthionoester, N-alpha-Fmoc-O-benzyl-threonine-O-trimethylsilylthionoester, and N-alpha-Fmoc-threonine-O-trimethylsilylthionoester.

Further embodiments include the synthesis of simple as well as complex cyclic and acyclic peptides, the construction of glycopeptides, for peptide ligation, for protein thiol ester functionalization as well as for commercial peptide synthesis.

In certain embodiments, the disclosure relates to methods of making an amide bond comprising mixing a compound with a carboxylic acid group, a silylating agent with a thiol group, and a primary or secondary amino under conditions such that an amide is formed. A typical silylating agent with a thiol group is hexamethyldisilathiane.

The reagents may also be employed to ligate an amino acid, peptide or protein group to a carbohydrate group, which may be a mono-, di-, tri- or polysaccharide, or to a nucleoside. The reagents of this disclosure may also be employed to ligate an amino acid, a peptide or protein group to a reporter group, tag or label (e.g., a group whose presence can be detected by optical or mass spectrometry or other instrumental method), including a fluorescent or phosphorescent group, an isotopic label or a radiolabel.

The chemistry of the present disclosure may be suitably employed for the formation of cyclic peptides as well for macrolactamization reactions.

In some embodiments, the disclosure relates to methods of making a compound with an amide bond comprising mixing an O-silylated thionoester and a primary or secondary amine under conditions such that an amide is formed.

In certain embodiments, the method further comprises the step of providing the O-silylated thionoester by mixing a compound with a thiolacid group, and a silylating agent under conditions such that an O-silylated thionoester is formed. In further embodiments, the silylating agent is in two, three, four, or five fold excess compared to the thiolacid. In certain embodiments, the reaction further comprises a base in two, three, four, or five fold excess compared to the thiolacid. In further embodiments, the base is a secondary or tertiary amine.

In certain embodiments, the silylating agent is selected from the group consisting of trimethylsilanecarbonitrile, bis(trimethylsilyl)acetamide, and phenylchlorosilane.

In certain embodiments, the method further comprises the step of providing a compound with a thiolacid group by i) mixing a compound with a carboxylic acid group and a coupling reagent providing an activated carboxylic acid and ii) mixing the activated carboxylic acid and a thiol nucleophile providing a compound with at thiolacid group. In further embodiments, the coupling reagent is selected from the group consisting of dicyclohexylcarbodiimide or isopropyl chlorocarbonate. In further embodiments, the thiol nucleophile is selected from the group consisting of sodium hydrogen sulfide and trimethylsilyl thiol. In further embodiments, the compound with a carboxylic acid group is an amino acid.

In certain embodiments, the method further comprises the step of providing the O-silylated thionoester by mixing a compound with a carboxylic acid group, disulfide, and a phosphine under conditions such that an O-silylated thionoester is formed. In further embodiments, the disulfide is bis trimethylsilyl disulfide.

In certain embodiments, the disclosure relates to methods of making an amide bond comprising mixing an compound with a thiolacid group, a silylating agent, and a primary or secondary amine under conditions such an amide is formed.

In certain embodiments, the disclosure relates to the reaction of carboxylic acids, esters or S- or O-silylthiolate with aluminum silylthiolate and an amine under conditions such that an amide is formed.

In certain embodiments, the disclosure relates to mixing a carbon nucleophile with O-silylthionoester under conditions such that a ketone is formed. In further embodiments, the nucleophile is an alkyl from an alkyl boronic acid ester or an alkyl from an alkyl stannane which react via a copper catalyzed reaction of O-silylthionoester with alkyl boronic acids (esters) or alkyl stannanes.

In certain embodiments, the disclosure contemplates S-silylthiol esters and O-silylthionoesters disclosed herein for use reactions with amines and carboxylic acids with silylthiols to form amides. Typically, the method comprises mixing a carboxylic acid, ammonia, primary or secondary amine with a silylthiol under conditions such that an amide is formed. Optionally, the silylthiol is conjugated to a solid support such as a bead, glass, or polymer. Optionally, a Lewis base is utilized.

In certain embodiments, the disclosure contemplates preparation of esters by the catalysis of carboxylic acids and alcohols with silylthiol esters. Typically, the method comprises mixing an alcohol and carboxylic acid with silylthiol under conditions such that an ester is formed. Optionally, a Lewis base is utilized.

In certain embodiments, the disclosure relates to a substrate linked to a silylthiol catalyst. Typically the substrate is a bead, glass, or polymer and the silylthiol catalyst comprises two aryl or branched alkyl groups attached to the silicon atom.

In certain embodiments, the disclosure relates to a method of preparing an amide bond comprising mixing a carboxylic acid and ammonia, a primary or secondary amine and a silicon thiol catalyst under conditions such that an amide is formed.

In certain embodiments, the disclosure relates to methods of preparing thionoesters comprising mixing a thiolacid, a silylating agent and a metal catalyst under conditions such that hydrogen and a thionoester is formed.

In certain embodiments, the disclosure relates to compositions and methods as provided in any of the figures; for the carboxylic acids $R^1$ may be alkyl, aryl, carbocyclyl, or heterocyclyl wherein $R^1$ may be optionally substituted with one or more, the same or different $R^4$;

for the amines $R^2$ and $R^3$ may be alkyl, alkenyl, hydroxy, amino, carbocyclyl, aryl, and heterocyclyl wherein $R^2$ and $R^3$ is optionally substituted with one or more, the same or different $R^4$;

$R^4$ is alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^4$ is optionally substituted with one or more, the same or different $R^5$.

$R^5$ is alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different $R^6$.

$R^6$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

for the silylating agent the R or R' may be alkyl, alkoxy, aryl, carbocyclyl, heterocyclyl, or two R or R' together may form a ring wherein R or R' may be substituted with one or more, the same or different, R'';

R'' is alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R'' is optionally substituted with one or more, the same or different, R'''; and R''' is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, any of the silylthiol, silylthionoesters, or thionoesters disclosed herein may comprise one or more substituents.

In certain embodiments, the disclosure relates to methods of making O-silylthionoesters comprising mixing a carboxylic acid, a silyl thiol, and a triflate catalyst under conditions such that an O-silylthionoester is formed. In certain embodiments, the triflate catalyst is an aniline salt substituted with one or more halogens such as pentafluoroanilinium trifluoromethane sulfonate. In certain embodiments the silylthiol is triphenyl silylthiol optionally substituted with one or more substituents such as halogen, alkyl, or alkoxy substituents.

In certain embodiments, the disclosure contemplates the reaction of $(alkoxy)_3SiSH$ and a carboxylic acid under conditions such that a O-silylthionoester is formed. In certain embodiments $(alkoxy)_3SiSH$ is $(tBuO)_3SiSH$.

Other compositions, methods, features, and advantages of the present disclosure will be or become apparent to one with skill in the art upon examination of the following drawings and detailed description. It is intended that all such additional compositions, methods, features, and advantages be included within this description, be within the scope of the present disclosure, and be protected by the accompanying claims.

BRIEF DESCRIPTION OF THE FIGURES

FIG. 3 illustrates alternative methods for producing O-silylthionoesters.

FIG. 4 illustrates silylative verses traditional activation of a thiol acid.

FIG. 5 shows data provided for experiments. a Isolated yield; the epimerization ratio was determined by HPLC. b A solution of 1 equiv of Cbz-Gly-SH and 1 equiv of BSA in THF was added to a solution of 1 equiv of Cbz-L-Arg-OH, 1.3 equiv of L-Phe-OMe.HCl and 1.3 equiv of triethylamine. The reaction mixture was stirred at room temperature for 10 h. c To a THF solution of 1 equiv dipeptidic thiol acid, 1.1 equiv PhSiH2Cl, 1.3 equiv amino ester hydrochloride salt was added 2.3 equiv DIEA stirred at room temperature for 8 or 15 h. d To a THF solution of 1 equiv of dipeptidic thiol acid, 1.1 equiv PhSiH2Cl, 2 equiv amino acid ester hydrochloride salt was added 3.0 equiv DIEA stirred at room temperature for 15 h.

FIGS. 6A-D illustrate certain embodiments of the disclosure.

FIGS. 7A-C illustrate certain embodiments of the disclosure.

FIGS. 8A-B illustrate certain embodiments of the disclosure.

FIG. 10 shows results from experiments performed to form O-silylthionoesters.

DETAILED DESCRIPTION

Terms

Figure 1:
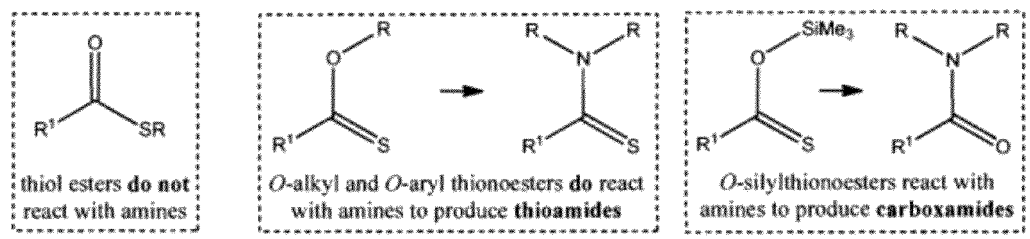
FIG. 1 illustrates different reaction profiles of amines with thiol esters and O-organothionoesters, and of amines with O-silylthionoesters under the same reaction conditions providing an amide product.

As used herein, the term "amino acid" refers to both naturally-occurring and synthetically modified (D-, L-, achiral or racemic) amino acids and derivatives. In some embodiments, the amino acid may be selected from the group consisting of any one or more of (D-, L-, achiral or racemic) glycine, alanine, valine, leucine, isoleucine, phenylalanine, serine, methionine, proline, tyrosine, tryptophan, lysine, arginine, histidine, aspartate, glutamate, asparagine, glutamine, cysteine, methionine, hydroxyproline, gama-carboxyglutamate, O-phosphoserine, ornithine, homoarginine and various protected derivatives thereof.

A "protecting group" refers to those moieties that are introduced into a molecule by chemical modification of a functional group in order to obtain chemoselectivity in a subsequent chemical reaction. Examples include, but are not limited to , 4-methoxy-2,3,6-trimethylphenyl)sulfonyl (Mtr), 2,2,5,7,8-pentamethyl-chroman-6-sulphonyl (Pmc), tosyl (Tos), mesitylenesulfonyl (Mts), 4,4'-dimethoxybenzhydryl (Mbh), 2,4,6-trimethoxybenzyl (Tmob), tripheylmethyl (Trt), 9-fluorenylmethyloxycarbonyl (fmoc), tert-buty (tBu), benzyl (Bzl), t-Butoxymethyl ether (Bum), (2,4-dinitrophenol) Dnp, benzyloxymethyl (Bom), benzyloxycarbonyl (Z), 2-chloro-benzyloxycarbonyl (CIZ), t-butyloxycarbonyl (Boc), formyl (CHO) or 2-bromobenzyloxycarbonyl (BrZ) and heterocycles such as succinimide, maleimide, and phathalimide.

As used herein, a "linker" refers to any molecular configuration that joins molecular moieties. It includes molecules with covalent and non-covalent interactions. A prefer linker is a polymer, i.e., molecule with repeated linking moieties. The linked moieties may be identical in structure or vary, e.g., copolymers. Linking polymers include, but are not limited to, biological polymers, polyethylene glycols, alkylacrylates, alkylacrylamides, and substituted variants.

"Saccharide" refers a sugar(s) or substituted sugar(s) exemplified by, but not limited to, ribose, riboside, glucose, glucoside, mannose, mannoside, mannoside, galactose, galactoside, talitol, taloside, rhamnitol, rhamnoside, maltose, maltoside, 2,3-dideoxyhex-2-enopyranoside, 2,3-desoxy-2, 3-dehydroglucose, 2,3-desoxy-2,3-dehydroglucose diacetate, 2,3-desoxy-2,3-dehydromaltoside, 2,3-desoxy-2,3-dehydromaltoside pentaacetate, 2,3-desoxymaltoside, lactoside, lactoside tetraacetate, 2,3-desoxy-2,3-dehydrolactoside, 2,3-desoxy-2,3-dehydrolactoside pentaacetate, 2,3-desoxylactoside, glucouronate, N-acetylglucosamine, fructose, sorbose, 2-deoxygalactose, 2-deoxyglucose, maltulose, lactulose, palatinose, leucrose, turanose, lactose, mannitol, sorbitol, dulcitol, xylitol, erythritol, threitol, adonitol, arabitol, 1-aminodulcitol, 1-aminosorbitol, isomaltitol, cellobiitol, lactitol, maltitol, volemitol perseitol, glucoheptitiol, alpha, alpha-glucooctitiol or combinations thereof, i.e., disaccharides, polysaccharides, and carbohydrates. Saccharides can be derivatized with molecular arrangements that facilitate synthesis (i.e., contain a protecting group, e.g., acetyl group).

The term "substrate" refers to any variety of solid surfaces. The solid surfaces may be provided in a variety of formats. For examples, the substrates may be planar or curved surfaces or be beads. In some preferred embodiments, the beads are commercially available beads such as glass beads, agarose beads, acrylic beads, plastic, or latex beads. In some embodiments, the beads are magnetic. In still other embodiments, the beads are coated with organic film(s) or metal(s) such as silver or gold. A wide variety of reaction types are available for the functionalization of solid surfaces. For example, solid surfaces constructed of a plastic such as polypropylene, can be surface derivatized by chromic acid oxidation, and subsequently converted to hydroxylated or aminomethylated surfaces. Substrates made from highly crosslinked divinylbenzene can be surface derivatized by chloromethylation and subsequent functional group manipulation. Additionally, functionalized solid surfaces can be made from etched, reduced polytetrafluoroethylene. When the solid surfaces are constructed of a siliceous material such as glass, the surface can be derivatized by reacting the surface Si—OH, Si—H, and/or Si—Si groups with a functionalizing reagent. When the substrate is made of a metal film, the surface can be derivatized with a material displaying avidity for that metal.

A "silylating agent" refers to an variety of silicon based reagents typically used to form a silicon bond with atoms such as oxygen, nitrogen, and sulfur, including, but not limited to, N-methyl-N-(trimethylsilyl)trifluoroacetamide, N-tert-butyldimethylsilyl-N-methyltrifluoroacetamide, 1,3-bis(chloromethyl)-1,1,3,3-tetramethyldisilazane, 1-(trimethylsilyl) imidazole, 3-trimethylsilyl-2-oxazolidinone, allyl(chloro) dimethylsilane, bromotrimethylsilane, chlorotriethylsilane, chlorotriisopropylsilane, chlorotrimethylsilane, hexaethyldisiloxane, hexamethyldisilazane, N,N'-bis(trimethylsilyl) urea, N,N-dimethyltrimethylsilylamine, N,O-bis(trimethylsilyl)acetamide, N-methyl-N-trimethylsilylacetamide, N-methyl-N-trimethylsilylheptafluorobutyramide, trimethylsilyl methanesulfonate, trimethylsilyl N,N-dimethylcarbamate, trimethylsilyl trifluoromethanesulfonate, triphenylsilane, methyl 3-trimethylsiloxy-2-butenoate, phenylchlorosilane, or triethylsilane or mixtures thereof.

In certain embodiments, the silylating agent is intended to include molecules comprising of Si—S units such as silylthiols and silathianes, e.g., hexamethyldisilathiane (HMDST). Cyclic silathianes are similar in structure to HMDST and prepared in various ring sizes from starting materials provided in Kückmann et al., Inorganic Chemistry, 2005. 44(10): p. 3449-3458 and Gareau et al., Tetrahedron, 2001. 57(27): p. 5739-5750.

As used herein, "alkyl" means a noncyclic straight chain or branched, unsaturated or saturated hydrocarbon such as those containing from 1 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butyryl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and, the like, where optionally one or more pair of substituents together with the atoms to which they are bonded form a 3 to 7 member ring.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—CH3).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, propoxy, n-butoxy, s-butoxy, t-butoxy.

"Alkylamino" refers an alkyl group as defined above with the indicated number of carbon atoms attached through an amino bridge. An example of an alkylamino is methylamino, (i.e., —NH—CH3).

"Alkanoyl" refers to an alkyl as defined above with the indicated number of carbon atoms attached through a carbonyl bride (i.e., —(C═O)alkyl).

"Alkylsulfonyl" refers to an alkyl as defined above with the indicated number of carbon atoms attached through a sulfonyl bridge (i.e., —S(═O)2alkyl) such as mesyl and the like, and "Arylsulfonyl" refers to an aryl attached through a sulfonyl bridge (i.e., —S(═O)2aryl).

"Alkylsulfamoyl" refers to an alkyl as defined above with the indicated number of carbon atoms attached through a sulfamoyl bridge (i.e., —NHS(═O)2alkyl), and an "Arylsulfamoyl" refers to an alkyl attached through a sulfamoyl bridge (i.e., (i.e., —NHS(═O)2aryl).

"Alkylsulfinyl" refers to an alkyl as defined above with the indicated number of carbon atoms attached through a sulfinyl bridge (i.e. —S(═O)alkyl).

The term "substituted" refers to a molecule wherein at least one hydrogen atom is replaced with a substituent. When substituted, one or more of the groups are "substituents." The molecule may be multiply substituted. In the case of an oxo substituent ("═O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(═O)Rb, —NRaC(═O)NRaNRb, —NRaC(═O)ORb, —NRaSO2Rb, —C(═O)Ra, —C(═O)ORa, —C(═O)NRaRb, —OC(═O)NRaRb, —ORa, —SRa, —SORa, —S(═O)2Ra, —OS(═O)2Ra and —S(═O)2ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

The terms "cycloalkyl" and "cycloalkenyl" refer to mono-, bi-, or tri homocyclic ring groups of 3 to 15 carbon atoms which are, respectively, fully saturated and partially unsaturated. The term "cycloalkenyl" includes bi- and tricyclic ring systems that are not aromatic as a whole, but contain aromatic portions (e.g., fluorene, tetrahydronapthalene, dihydroindene, and the like). The rings of multi-ring cycloalkyl groups may be either fused, bridged and/or joined through one or more spiro unions. The terms "substituted cycloalkyl" and "substituted cycloalkenyl" refer, respectively, to cycloalkyl and cycloalkenyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, and the like.

The terms "halogen" and "halo" refer to fluorine, chlorine, bromine, and iodine.

The term "aroyl" refers to an aryl group (which may be optionally substituted as described above) linked to a carbonyl group (e.g., —C(O)-aryl).

An unspecified "R" group is a lower alkyl, alkoxy, or phenyl which may be optionally substituted with one or more substituents.

Throughout the specification, groups and substituents thereof may be chosen to provide stable moieties and compounds.

Amide Synthesis

The disclosure relates to methods for producing amide bonds and reagents related thereto. In certain embodiments, the disclosure relates to methods of producing an amide comprising mixing an O-silylated thionoester and an amine under conditions such that an amide is formed. In another embodiment, the disclosure relates to mixing a thiolacid, a silylating agent, and an amine under conditions such that an amide is formed.

Figure 2:
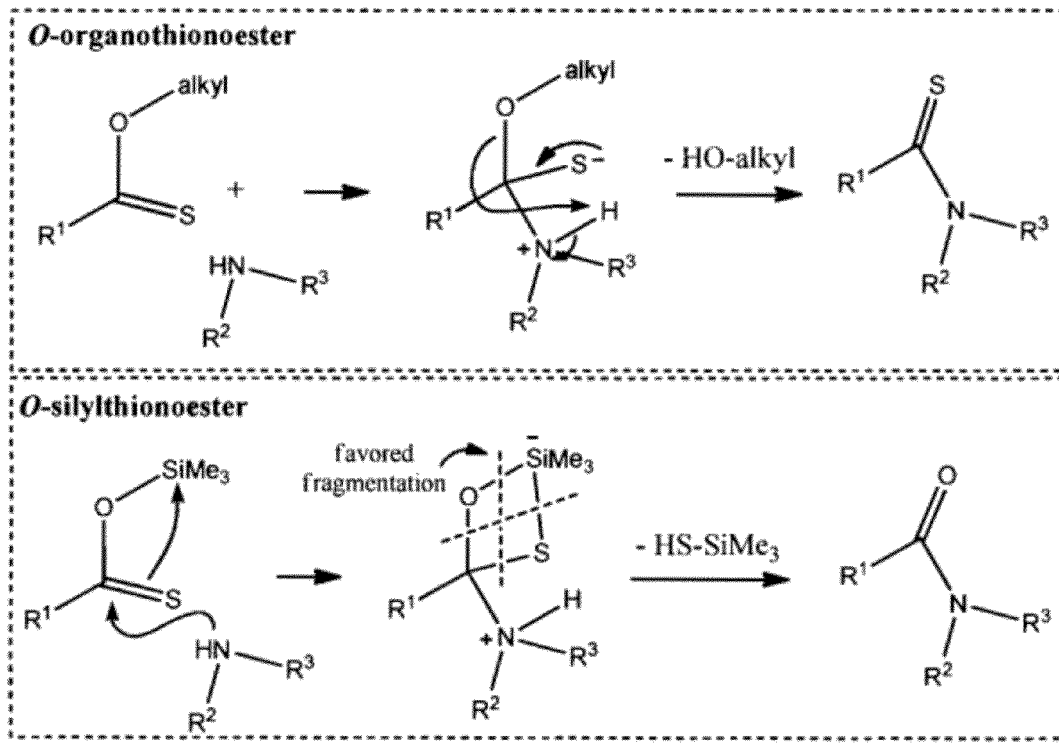
FIG. 2 illustrates the proposed mechanistic explanation for the reaction of an amine with O-organothionoesters and the O-silylthionoesters.

Although it is not intended that embodiments of the disclosure be limited by any particular mechanism, the chemistry is believed to be specific to O-silylated thionoester, since the structurally related O-alkyl and O-aryl thionoesters are known to react with amines to produce thioamides, rather than carboxamides (Glass, 2005, Science of Synthesis, 22:85-108). (see FIG. 1). Furthermore, under similar reaction conditions thiol esters do not react with amines to form amides. It was an unexpected discovery that O-silyl thionoesters form amide bonds upon reaction with amines. (See FIG. 1). It is believed that thionoesters react with nucleophiles via tetrahedral intermediates. The unique reactivity of the O-silyl thionoester is believed to be a function of the triorganosilyl group intercepting the sulfur anion generated by attaching the C=S bond of the O-silyl thionoester. (See FIG. 2). Fragmentation of the silyl-modified tetrahedral intermediate then favors formation of the oxoamide and HS—SiMe$_3$. The presence of the triorganosilyl moiety diverts the thionoester reactivity away from the thioamide pathway to the carboxamide pathway. (See FIG. 2).

The generation of the O-silyl thionoester may be achieved from carboxylic acid derivatives by a variety of available methods which are readily available to one skilled in the art. (Wojnowski et al., 2008, Zeitschrift fuer Anorganische and Allgemeine Chemie, 634; Martel et al., 1966, Comptes Rendus des Seances de l'Academie des Sciences, Series C: Sciences Chimques, 263:74-76; Kato et al., 1973, Bull. Chem. Soc. Jpn., 46:244-248; Kricheldorf et al., 1972, Makromolekulare Chemie, 158:223-239; Ishii and Nakayama, 2005, Comprehensive Organic Functional Group Transformations II, Vol 5, 459-491). Starting materials and reagents for the reactions depicted herein are available either from commercial sources or by use of known synthetic methods or by adaptation of known synthetic methods. The O-silylthionoesters may be isolated or generated in situ. Representative non-limiting examples include transformation from a carboxylic acid by mixing with an activating agent(s), such as carbodiimides and a thiol nucleophile followed by mixing with a silylating agent; by thiol ester formation by mixing a carboxylic acid, disulfide, and a phosphine, such as triphenylphosphine, and a silyl disulfide or thio phthalimide or succinimide such as 2-(trimethylsilylsulfanyl)isoindole-1,3-dione, 1-(trimethylsilylsulfanyl)pyrrolidine-2,5-dione; or by thio ester exchange, e.g., mixing a thio ester with a trimethylsilyl thiol. (See FIG. 3).

EXPERIMENTAL

Example 1

Amide Bond Construction

Amide bond construction was demonstrated starting with the thiol acid which was converted into the O-silylthionoester in situ by treatment with bis(trimethylsilyl)acetamide or trimethylsilanecarbonitrile. The method of activation tolerates a variety of protecting groups and functionalities, and is efficient with otherwise difficult sterically-hindered linkages.

| Entry | Time (h) | Product | Yield |
|-------|----------|---------|-------|
| 1 | 3 | *N-allyl benzamide* | 91 |
| 2 | 3 | *N-benzyl benzamide* | 89 |
| 3 | 3 | *N-(2-hydroxyethyl)benzamide* | 76 |
| 4 | 3 | *N-cycloheptylnicotinamide* | 70 |
| 5 | 3 | *N-(furan-3-ylmethyl)acetamide* | 82 |
| 6 | 5 | *phenyl(piperidin-1-yl)methanone* | 74 |
| 7 | 5 | *N-benzyladamantane-1-carboxamide* | 65 |

17
-continued
| Entry | Time (h) | Product | Yield |
|---|---|---|---|
| 8 | 11 | 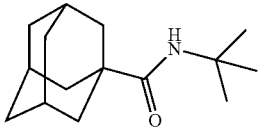 [SMILES: CC(C)(C)NC(=O)C12CC3CC(CC(C3)C1)C2] | 46 |
| 9 | 24 | 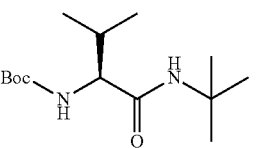 | 71 |
| 10 | 15 | 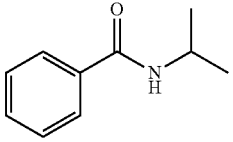 | 78 |
| 11 | 15 | 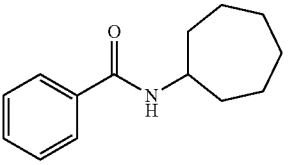 [SMILES: O=C(NC1CCCCCC1)c1ccccc1] | 80 |
| 12 | 24 | 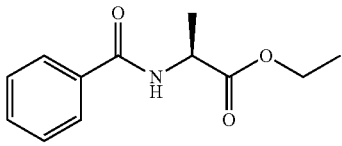 [SMILES: CCOC(=O)[C@H](C)NC(=O)c1ccccc1] | 88 |
| 13 | 24 | 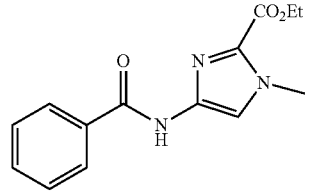 [SMILES: CCOC(=O)c1nc(NC(=O)c2ccccc2)cn1C] | 64 |
| 14 | 15 | 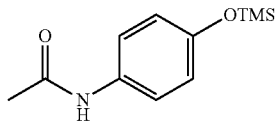 | 72 |
18
-continued
| Entry | Time (h) | Product | Yield |
|---|---|---|---|
| 15 | 20 | 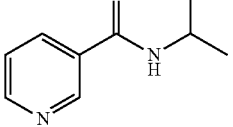 | 72 |
| 16 | 24 | 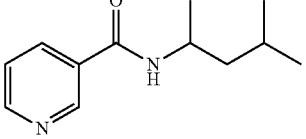 | 91 |
| 17 | 15 | 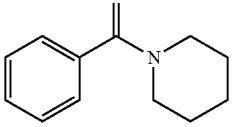 | 89 |
| 18 | 15 | 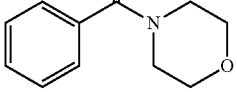 | 91 |
| 19 | 24 | 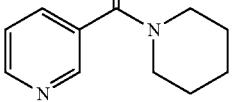 | 94 |
| 20 | 24 | 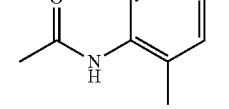 | 10 |
| 21 | 24 | 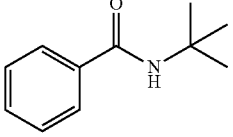 | 28 |
Example 2
Peptide Bond Construction
The reaction was also performed on some amino acids to illustrate the formation of peptide bonds. These results are depicted in the table below.

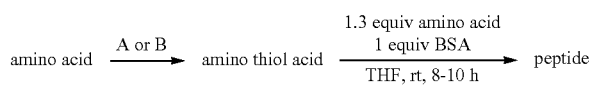
A: i) Fm-SH, DCC, DMAP then ii) piperidine, DMF
B: i) N-hydroxysuccinimide, DCC, CH$_2$Cl$_2$ then ii) NaHS, Dioxane
Fm is 9-fluorenylmethyl
BSA, N,O-bis(trimethylsilyl)acetamide
| Entry | Amino Thioacid (yield) | Peptide | Time (h) | Yield |
|---|---|---|---|---|
| 1 | Method B: 72% | | 8 | 90 |
| 2 | Method B: 72% | | 10 | 73 |
| 3 | Method B: 72% | | 10 (16$^a$) | 79 (74$^a$) |
| 4 | Method B: 72% | | 10 | 60 |
| 5 | Method B: 72% | | 19 | 71 |
| 6 | Method B: 75% | | 8 | 72 |
| 7 | Method B: 75% | | 10 | 61 |

-continued
amino acid →(A or B)→ amino thiol acid →(1.3 equiv amino acid, 1 equiv BSA, THF, rt, 8-10 h)→ peptide
A: i) Fm-SH, DCC, DMAP then ii) piperidine, DMF
B: i) N-hydroxysuccinimide, DCC, CH$_2$Cl$_2$ then ii) NaHS, Dioxane
Fm is 9-fluorenylmethyl
BSA, N,O-bis(trimethylsilyl)acetamide
| Entry | Amino Thioacid (yield) | Peptide | Time (h) | Yield |
|---|---|---|---|---|
| 8 | 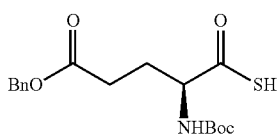 Method B: 75% | 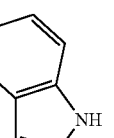 | 10 | 52 |
| 9 | 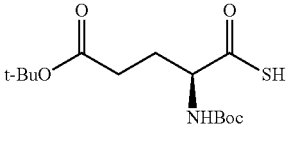 Method A: 81% | 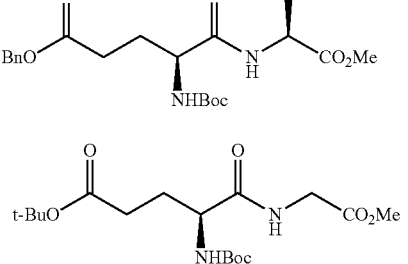 | 10 | 68 |
| 10 | 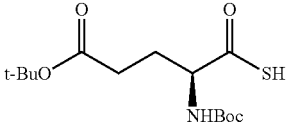 Method A: 81% | 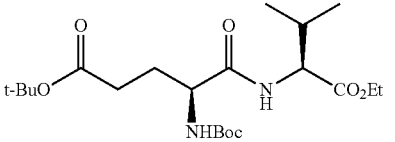 [SMILES: CCOC(=O)[C@@H](NC(=O)[C@H](CCC(=O)OC(C)(C)C)NC(=O)OC(C)(C)C)C(C)C] | 10 | 63 |
| 11 | 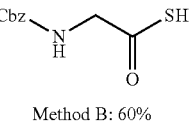 Method B: 60% | 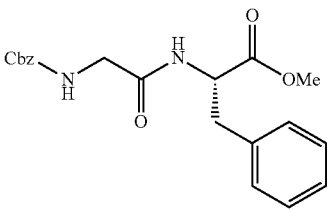 [SMILES: COC(=O)[C@H](Cc1ccccc1)NC(=O)CNC(=O)OCc1ccccc1] | 10 | 89 |
| 12[b] | 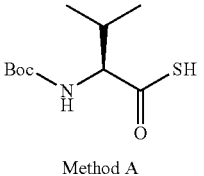 Method A | 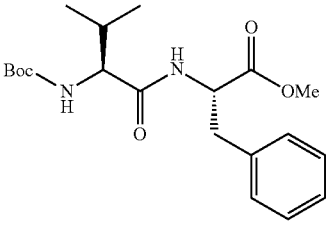 [SMILES: COC(=O)[C@H](Cc1ccccc1)NC(=O)[C@@H](NC(=O)OC(C)(C)C)C(C)C] | 63 | 67 |
| 13 | 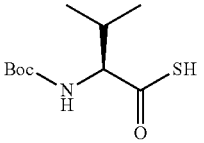 Method A: 82% | 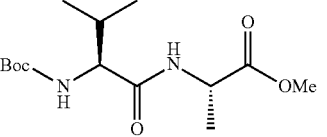 [SMILES: COC(=O)[C@H](C)NC(=O)[C@@H](NC(=O)OC(C)(C)C)C(C)C] | 53 | 55 | amino acid →(A or B) amino thiol acid →(1.3 equiv amino acid, 1 equiv BSA, THF, rt, 8-10 h) peptide A: i) Fm-SH, DCC, DMAP then ii) piperidine, DMF
B: i) N-hydroxysuccinimide, DCC, CH$_2$Cl$_2$ then ii) NaHS, Dioxane Fm is 9-fluorenylmethyl
BSA, N,O-bis(trimethylsilyl)acetamide

| Entry | Amino Thioacid (yield) | Peptide | Time (h) | Yield |
|---|---|---|---|---|
| 14 | 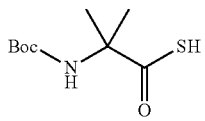 Method A: 80% | 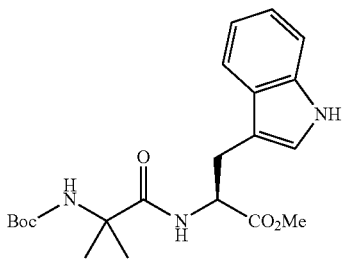 [SMILES: COC(=O)[C@H](Cc1c[nH]c2ccccc12)NC(=O)C(C)(C)NC(=O)OC(C)(C)C] | 10 | 23 |
| 15[b] | 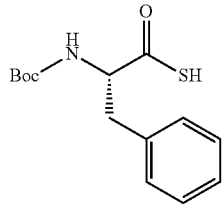 Method A | 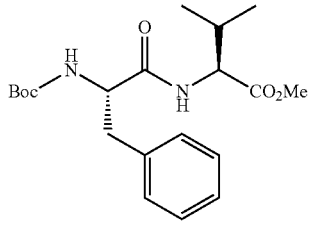 [SMILES: COC(=O)[C@@H](NC(=O)[C@H](Cc1ccccc1)NC(=O)OC(C)(C)C)C(C)C] | 18 | 70 |
| 16[b] | 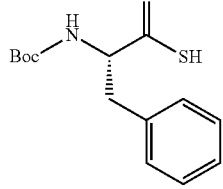 Method A | 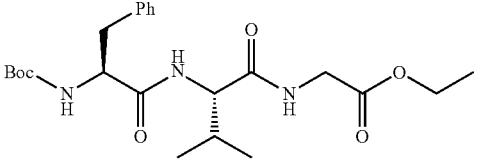 [SMILES: CCOC(=O)CNC(=O)[C@@H](NC(=O)[C@H](Cc1ccccc1)NC(=O)OC(C)(C)C)C(C)C] | 19 | 60 |
| 17c | | 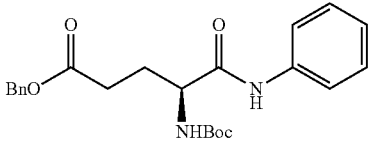 [SMILES: CC(C)(C)OC(=O)N[C@@H](CCC(=O)OCc1ccccc1)C(=O)Nc1ccccc1] | 24 | 69 |

[a] condition for the reaction: 1 equiv thiol acid, 1 equiv Cbz-Arg-OH, 1.3 equiv HCl•Val-OMe, 1.3 equiv NEt$_3$, 1 equiv BSA, stirred at rt for 16 h;

[b] thiol acids were used directly after removing Fm group from Fm-thiol acids without purification.

c No racemization was observed

Example 3

Tripeptide Epimerization Test

Of particular significance with regard to peptide ligation is the low level of epimerization displayed in the Anderson epimerization test (compared to ~35% with DCC). See Anderson & Callahan (1959) Journal of the American Chemical Society, 1958. 80(11): p. 2902-2903.

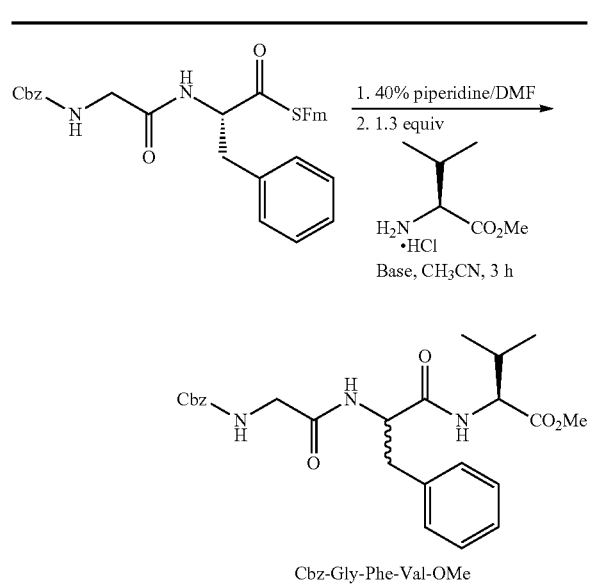

Cbz-Gly-Phe-Val-OMe

| Entry | Conditions | Diastereomeric Ratio |
|---|---|---|
| 1 | 1.0 equiv BSA, 1.3 equiv N-methylmorpholine (NMM), rt | 19:1 |
| 2 | 1.0 equiv BSA, 1.3 equiv DIEA, rt | 22:1 |
| 3 | 5.0 equiv BSA, 1.3 equiv DIEA, rt | 27:1 |
| 4 | 5.0 equiv BSA, 1.3 equiv DIEA, 50° C., rt | 24:1 |
| 5 | 1.1 equiv PhSiH$_2$Cl, 2.3 equiv DIEA, rt | 35:1 |

Example 4

Variation of the Si Unit with Respect to Epimerization-free Peptide Ligation Lower epimerization levels in the Anderson test were observed by modifying reaction conditions. Additionally, effects are also observed by altering the silyl protecting group. For example, larger Si units such as triisopropylsilyl (TIPS) form the reactive O-silylthionoester species, which generate the amide product, but much slower than trimethylsilyl units. Epimerization levels can be lowered by enhancing the S to O silatropic migration, which is believe to be the rate limiting step of the reaction. One explores a series of Si units of various steric dimensions and electronic nature.

Example 5

Generation of S-silylthiol Ester In Situ from Carboxylic Acid

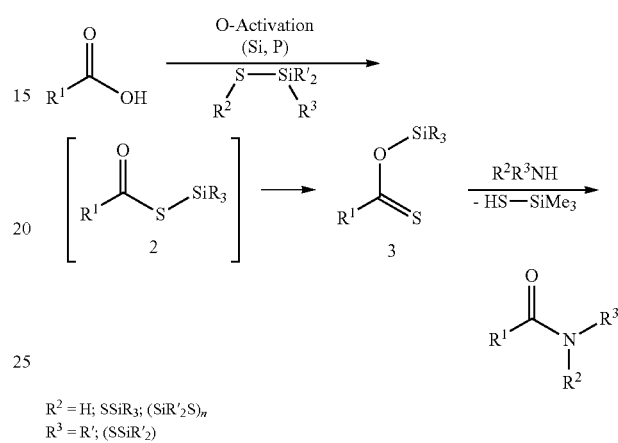

$R^2$ = H; SSiR$_3$; (SiR'$_2$S)$_n$
$R^3$ = R'; (SSiR'$_2$)

It was observed that HMDST (Procedure A below) was an important component through control experiments. No formation of product was observed in reactions that substitute BSA for HMDST.

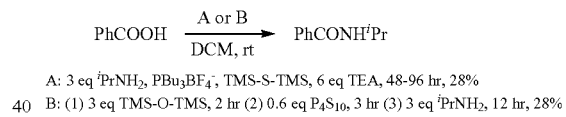

A: 3 eq $^i$PrNH$_2$, PBu$_3$BF$_4^-$, TMS-S-TMS, 6 eq TEA, 48-96 hr, 28%
B: (1) 3 eq TMS-O-TMS, 2 hr (2) 0.6 eq P$_4$S$_{10}$, 3 hr (3) 3 eq $^i$PrNH$_2$, 12 hr, 28%

The most direct means of thiosilyl introduction to carboxylic acid would utilize reagents that contain both a silicon and sulfur moiety such as silylthiols, bis-silyl disulfides, or disilathianes in conjunction with benign oxygen acceptor. Currently, there are two silylthiols and one disilathiane commercially available. A variety of these agents, as well as bis-silyl disulfides, are produced from starting materials. Kükmann et al., Inorganic Chemistry, 2005. 44(10): p. 3449-3458. Gareau et al., Tetrahedron, 2001. 57(27): p. 5739-5750.

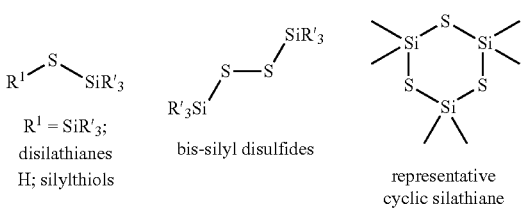

$R^1$ = SiR'$_3$; disilathianes
H; silylthiols bis-silyl disulfides representative cyclic silathiane With regard to the stoichiometric source of oxygen acceptor, initial success was found using commercially available tributyl phosphine and silicon based reagents. A variety of trisubstituted phosphines, such as trialkylphosphines or triarylphosphines may be utilized.

Example 6

Generation of Aluminum Silylthiolates

In certain embodiments, the disclosure relates to the reaction of aldehydes, carboxylic acids, or esters with aluminum silylthiolate and an amine under conditions such that an amide is formed via an S- or O-silylthiolate intermediate. One utilizes dimethylaluminum silylthiolates in a Tishchenko-type reaction. See Fujiwara and Kambe, Thio-, Seleno-, and Telluro-Carboxylic Acid Esters, in Chalcogenocarboxylic Acid Derivatives, S. Kato, Editor. 2005, Springer Berlin/Heidelberg p. 87-140. One prepares dimethylaluminum silylthiolates following the same procedures with silylthiols from trimethylaluminum (or $AlMe_2Cl$) and alkyl thiols.

Example 7

Construction of a Cyclic D,L-a-peptide that has Exhibited Systemic Antibacterial Activity Against Methicillin-resistant *Staphylococcus aureus* Using Solid-phase Peptide Synthesis Protocol

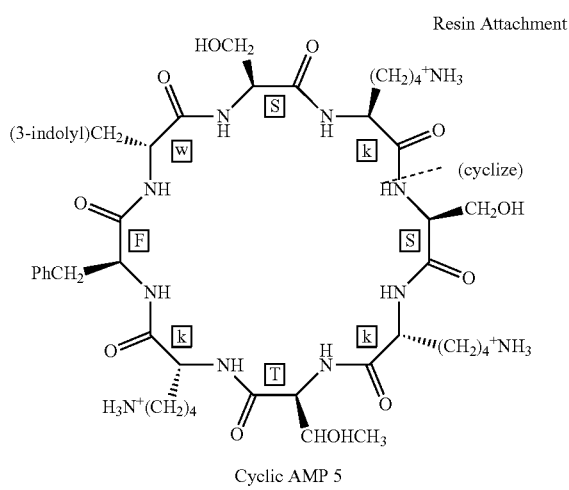

Cyclic AMP 5

One uses a trityl chloride polystyrene-based resin beads and standard Fmoc protocols to elongate a peptide by addition of N-protected O-silylthionoesters. Attachment of side-chain functionalities to the solid surface is contemplated. Addition of a strong acid such as trifluoroacetic acid, a silylthiolate reagent, or by a dialkylaluminum silylthiolate, results in cleavage of the peptide. Compound 5 is provided in Dartois et al., Antimicrob. Agents Chemother., 2005. 49(8): p. 3302-3310. Following the attachment of the first amino acid (N-alpha-Fmoc-D-Lys-allyl ester) to a resin (trityl chloride polysterene-based), one sequentially grows the peptide to resin-k-S-w-F-k-T-k-S (Uppercase letters=L-a-amino acid; Lowercase=D-a-amino acid) via repeated cycles of Fmoc deprotection, coupling with the appropriate N-protected O-silylthionoester amino acid by either in situ generation from carboxylic acid, or thiol acid generated species, and washing. One produces cyclic peptides by deprotecting the N-terminus of the resin-bound peptide followed by addition of silylthiolate reagent to the resin-bound C-terminus allyl ester.

Example 8

Synthesis of Non-natural Peptides

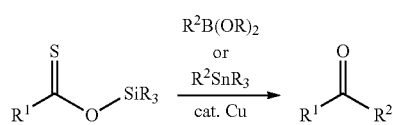

In certain embodiments, the disclosure relates to mixing a carbon nucleophile with O-silylthionoester under conditions such that a ketone is formed. In further embodiments, the nucleophile is an alkyl from an alkyl boronic acid ester or an alkyl from an alkyl stannane which react via a copper catalyzed reaction of O-silylthionoester with alkyl boronic acids (esters) or alkyl stannanes.

Example 9

Comparison to Traditional Peptide Coupling Protocol

A comparison of the reaction of Boc-L-Glu(O-tBu)—SH and Gly-OMe using a traditional peptide coupling protocol with the new silylative activation is both illustrative and compelling, demonstrating the unique reactivity of the O-silylthionoester approach to peptide construction. A 1:1.3 mixture of Boc-L-Glu(O-tBu)—SH and Gly-OMe.HCl was first exposed to Et3N to liberate the amine and then to 1 equiv of BSA in THF at room temperature to produce the peptide in 74% yield within 8 h. In contrast, traditional activation of the thiol acid with PyBop and DIEA gave a mixture of the desired peptide (40%) and the thioamide (28%) as depicted in FIG. 4.

Example 10

General Procedure for Peptide Synthesis

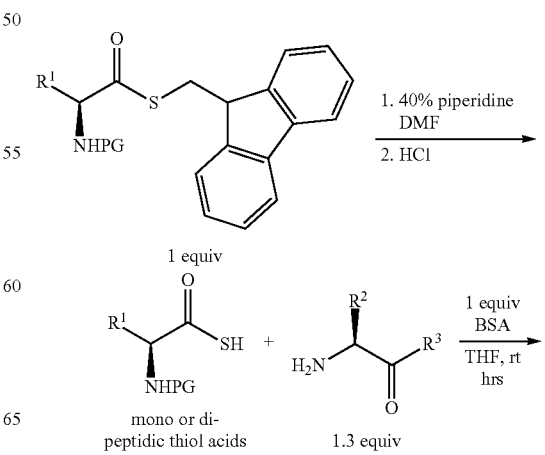

-continued

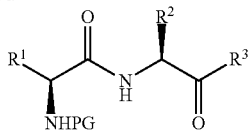

wherein $R^1$, $R^2$, and $R^3$ are provided in FIG. 5

A solution of 1 equiv of the N-protected α-amino thiol acid (generated from the corresponding 9-fluorenylmethyl thiol esters via piperidine deprotection-HCl acidification) and 1 equiv of BSA in THF was added to a solution of 1.3 equiv of the amino acid hy-drochloride salt and 1.3 equiv of triethylamine or diisopropylethylamine (DIEA) in THF. The mixture was then stirred at room temperature for 8-63 h.

The thiol acids were either available commercially or were prepared from the corresponding 9-fluorenylmethyl thiol esters via a standard piperidine deprotection-acidification protocol 11 and used without further purification. When the silylation of the thiol acid is carried out at room temperature in the presence of a primary or secondary amine, amide linkages are generated in very good yields within a matter of hours. Both aromatic thiol acids (entries 1-5) and aliphatic thiol acids (entries 6-10) reacted effectively with primary and secondary amines to produce secondary and tertiary amides, respectively. The hydroxyl group was well tolerated under the reaction conditions (entry 4). Even aniline of low nucleophilicity reacted smoothly with N-Boc-Glu thiol acid to produce the corresponding anilide (entry 7). Sterically hindered thiol acids and amines also reacted to provide the sterically congested amides in quite good yields (entries 8-10). Remarkably, doubly hindered amides were also obtained in good yields (entries 9, 10), although longer reaction times were required. No racemization was observed for entries 7 and 10.

Peptide bond formation was also easily accomplished using the silylative activation of N-protected α-amino thiol acids (FIG. 5). The peptidic thiol acids were generated from the corresponding 9-fluorenylmethyl thiol esters by the method of Crich et al., Org. Lett. 2007, 9, 4423-4426, hereby incorporated by reference in entirety, and used without further purification. As shown in FIG. 5, Gly, Met, Phe, Glu, and Pro thiol acid residues reacted smoothly to give the corresponding dipeptides (entries 1-9). It is noteworthy that sterically hindered α-amino thiol acids like Val (entries 10 and 11) and even 2-aminoisobutyric thiol acid (entry 12) are effectively coupled using this method, although longer reaction times were required to achieve acceptable yields. The amino acids, Phe, Tyr, Val, Ala, Gly, Met, Trp and Pro were all equally effective as N-terminal coupling partners (entries 1-15). The formation of Cbz-Gly-L-Tyr-OMe indicates that phenolic residues do not interfere with the coupling reaction (entry 2). Cbz-Gly-L-Phe-OMe, which is formed as a single dipeptide in 78% yield from Cbz-Gly-SH and L-Phe-OMe under the general coupling conditions (entry 1), is generated in almost an identical isolated yield (71%) when an equimolar amount of Cbz-L-Arg-OH is added to the reaction mixture. This simple experiment confirms the compatibility of this method with both carboxylic acid and guanidine functionalities.

Even prior to any extensive studies of the influence of electronic and steric effects of the silicon reagent, epimerization of sensitive stereocenters using the pH-neutral "silylative switch" protocol for peptide coupling is competitive with or better than existing technologies. For example, the absence of epimerization at both coupling partners was verified by HPLC analysis for the dipeptides shown in entries 1, 3-5 and for the tripeptide Boc-L-Phe-L-Pro-L-Ala-OEt in entry 13 of FIG. 5. Furthermore, both the Anderson (entry 14) and the Anteunis (entry 15) tests were conducted to evaluate epimerization-prone linkages during the peptide formation process. Of significance for future systematic studies of the influence of the silylating agent, PhSiH$_2$Cl gave lower levels of epimerization than BSA in the few cases preliminarily investigated. In the Anteunis test, this method gave less than 5% of epimerization, which is superior to results using DCC (DL % 18.8%) and PyBOP (DL % 6.6%) to facilitate the coupling between Z-Gly-L-Phe-OH and L-Val-OMe.HCl, as reported in Chen & Xu, *Tetrahedron Lett.*, 1992, 33, 647-650.

Example 11

Preparation of O-silylthionoesters

O—Silylthionoesters may be prepared by the salt elimination protocol (thioacid+ chlorosilane+Et$_3$N) using PhC(O)SH and CH$_3$C(O)SH and commercially available chlorosilanes (Me$_3$SiCl, Ph$_3$SiCl, PhMe$_2$SiCl, C$_6$F$_5$Me$_2$SiCl, i-Pr$_3$SiCl) as well as ((C$_6$F$_5$)$_3$SiCl, 4-NO$_2$C$_6$H$_4$Me$_2$SiCl, 4-MeOC$_6$H$_4$Me$_2$SiCl). Alternatively, the O-silylthionoesters may be prepared by the direct reaction of known silylthiols and acid halides. These chemistries provide access to O-silylthionoesters (Me$_3$SiOC(S)Ph), (R$_3$SiOC(S)Ph, R=t-BuO, R=Ph and R=2,6-XyO). (Het)Me$_2$SiO(C=S)Ar (where Het=2-pyridyl, 2-pyrimidinyl, 2-N-methylimidazolyl) may be used to provide proton transfer assisted enhanced reaction rates as suggested in FIG. 6A.

Functional group sensitivity may complicate the use of (N-hetero)dimethylsilyl chloride reactants, 2-pyridyl-Me$_2$SiCl in the construction of N-containing heteroaromatic silane derivatives by traditional salt elimination Si—S bond formations. As an alternative dehydrogenative coupling of a thioacid and a heteroaromatic silane, catalytic dehydrogenative approaches to S—Si bond formation may be used based on Rh, Pd, Fe, and trispentafluoro-phenylborane for the direct coupling of, for example, (2-pyridyl)Me$_2$SiH with thioacids RC(O)SH to generate the O-silylthionoester, (2-pyridyl)Me$_2$SiOC(S)R. See FIG. 6B.

Silylthionoesters as mild, activated carboxyl equivalents may be used in reactions with π-nucleophiles (electron-rich aromatics, enols, and enamines), ketoacids, carbanions, and organometallics. Representative nucleophilic partners are suggested in FIG. 6D.

Within certain embodiments, the disclosure contemplates R$_3$SiS— units that are non-volatile, recoverable/recyclable, and sufficiently stable to hydrolysis by water (i.e., i-Pr$_3$Si—SH, Ph$_3$SiSH, and tBuO$_3$SiSH, stable compounds, the latter two possessing significant stability to hydrolysis). One may prepare silicon reagents that are sterically shielded at silicon, such as 2-(6-methylpyridyl)Me$_2$Si, 2-(6-isopropylpyridyl)Me$_2$Si, and (2-pyridyl)iPr$_2$Si following procedures used to generate (2-pyridyl)Me$_2$SiH. TRMS-SH (TRMS=tris(2,2",6,6"-tetramethyl-m-terphenyl-5'-yl)silyl). See FIG. 7A.

In certain embodiments, the disclosure contemplates the preparation of S-silylthiol esters (and thus to O-silylthionoesters) directly from carboxylic acids (or esters) by reacting with silylthiols. Two silylthiols, iPr$_3$SiSH and Ph$_3$SiSH, are commercially available; the latter is an air-stable solid. Other silylthiols have been prepared in a variety of ways. Aryl silanes (Ar$_x$R$_y$SiH; x=1-3, y=0-2) as well as (PhCH$_2$)$_3$SiH can be converted to R$_3$SiSH by either direct reaction with S8 at elevated temperatures, or by radical mediated procedures utilizing phosphonium sulfide or COS.

Catalytic dehydrogenative approaches may be used to form silylthioethers from thiols and silanes or disilanes (catalysts: Rh, Pd, Fe, and B). Pd-catalyzed dehydrogenation of $Et_3Si-H$ with $H_2S$ directly generates $Et_3SiSH$. A sulfur congener of the remarkably stable TRMS family of stabilized silicon derivatives, TRMS-SH (TRMS=tris(2,2",6,6"-tetramethyl-m-terphenyl-5'-yl)silyl) may be prepared by reaction of the corresponding silane with elemental sulfur. See FIG. 7A)

The catalyzed silylthioesterification of carboxylic acids will generate water (FIG. 7B). The silylthioesterification approach to O-silylthionoesters utilizes hydrolytically stable triorganosilylthiols, such as the robust triisopropylsilylthiol (TIPS—SH), or TRMS-SH used in conjunction with dehydration catalysts based on boronic acids, onium Brønsted acids (which have been used in thioesterifications), and water-stable Lewis acids, such $Bi(OTf)_3$. TIPS—SH and TRMS-SH may be treated with benzoyl chloride to prepare the S-silylthioesters, TIPSSC(O)Ph and TRMS-SC(O)Ph. The S-silylthioesters will rearrange to their corresponding O-silylthionoesters, TIPS—OC(S)Ph and TRMS-OC(S)Ph. Effective migration from S to O of the hindered TIPS group was observed to generate a TIPS—OC(S)Ph thionoester effectively at room temperature in THF, benzene, and $CHCl_3$. In certain embodiments, the disclosure contemplates reacting TIPS— and TRMS-based O-silylthionoesters TIPS— and TRMS-OC(S)Ph with ammonia, primary or secondary amine nucleophiles and recovering TIPS—SH and TRMS-SH. The use of sulfur-selective Lewis acids is optionally contemplated (FIG. 7C). It is contemplated that the thionoesters may be enhanced by running reactions in toluene or other solvents at elevated temps, above 35(35-60° C.).

Hexamethyldisilathiane (HMDST: TMS-S-TMS) is an effective reagent for the thionation of carbonyl compounds. The catalyzed reaction of carboxylic acid trimethylsilyl esters with HMDST with unsymmetrical disilathianes are contemplated (FIG. 8A). Cyclotrisilathianes such as $(SSiMe2)_3$ that containing Si—S units similar in structure to HMDST are readily prepared from $Cl_2SiR_2$, Na metal, and elemental sulfur S. In certain embodiments, the disclosure contemplates the reaction of thioesters (RC(O)SMe) with S-triorganosilyl thiols and S-triorganosilyl trimethylsilyl ethers as an alternative generation of thionoesters.

Bistriorganosilyldisulfides may be prepared and used in a Mukaiyama-like redox dehydration approach to thiol esters. After S to O tautomerization of the triorganosilyl group, O-silylthionoesters may be formed (FIG. 8B). N-(triorganosilylthiyl) may be used for the synthesis of N-thioimides (from the corresponding thiol and N-chlorosuccinimide and by reaction of the corresponding disulfide with an N-bromoimide).

Example 12

Silanethiol-Catalyzed Amidation Reactions

Figure 9:
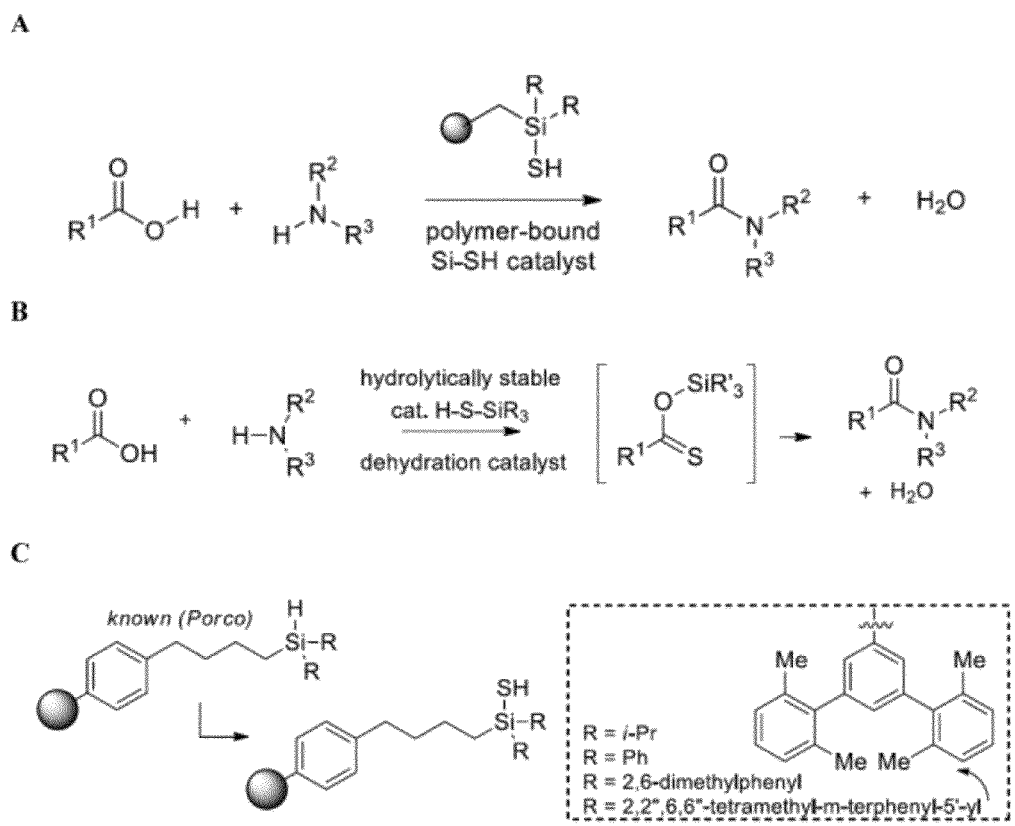
FIGS. 9A-C illustrate certain embodiments of the disclosure.

In certain embodiments, the disclosure contemplates the use of a silanethiol to form an amide or ester. The silanethiol may be on a solid support (FIG. 9A). TRMS-SH may be used as co-catalysts in the direct condensation of carboxylic acids with amines mediated by condensation catalysts based on boronic acids, onium Brønsted acids, and water-stable Lewis acids (FIG. 9B). Other sterically shielded silyl thiols maybe prepared (i.e., TDS=tris(2,6-diphenylbenzyl)silyl and TEDAMS=tris(extended diarylmethyl)silyl). A silicon variant of the TRMSSH is contemplated in co-catalyzed amidation.

Porco approach to polymer-supported silanes are contemplated in order to prepare solid-phase variants of TRMS-SH to facilitate (1) the ease of use and recycling of the catalytic silylthiol and (2) product purification (FIG. 9C). Merrifield resin may be treated with allylmagnesium chloride, then hydrosilylated to generate polymer-bound $PS-(CH_2)_4SiCl_2H$. Reaction with RMgX or RLi provides polymer-supported silanes, $PS-(CH_2)_4SiR_2H$, possessing variable steric shielding near the silicon (2,2",6,6"-tetramethyl-m-terphenyl-5'-yl Grignard reagent). Direct reaction of the silane with elemental sulfur (or a Pd-catalyzed dehydrogenation with $H_2S_{39}$) may be used to provide the solid supported silylthiols (polyhydroxysiloxanes react with RSH in the presence of a Rh catalyst to generate polymeric silylthio ethers). Hydrolysis-stable, solid-phase silylthiol catalysts are contemplated for use in amidations and esterifications.

Example 13

Dehydrative Condensation of Silylthiols and Carboxylic Acids via Ammonium Salt Catalysis The use of $Ph_3SiSH$ as a nucleophilic coupling partner in the dehydrative condensation of representative carboxylic acids has led to a one-step production of O-silylthionoesters, and a two-step, one-pot production of oxoamides (via addition of amine). This is the first example of utilizing ammonium salt catalysts for amide production from carboxylic acids, solely due to the unique method of carboxyl activation provided from the silylative migration. In the reaction, various $R_3SiSH$ were initially tested as nucleophiles with representative carboxylic acids, solvents, temperatures, and catalysts. It was observed that $Ph_3SiSH$ was uniquely effective in reactions employing refluxing xylenes and 10 mol % DPAT (diphenylammonium triflate) or PFPAT (pentafluorophenylammonium triflate). (See FIG. 10A)

Amide bond formation occurs upon addition of an amine to the cooled crude reaction mixture. A slight excess of amine (1.1 equiv) is used to quench the ammonium catalyst as well as serve as nucleophile. The in situ production of amide has been observed in 6-64% yield with a variety of RCOOH (FIG. 10B). $Ph_3SiSH$ may be viewed as a new stoichiometric "coupling reagent" used with catalytic ammonium salts to activate carboxylic acids for addition of various nucleophiles. The results also represent the first system to form O-silylthionoesters directly from RCOOH and a [Si—S] unit.

Example 14

Figure 11:
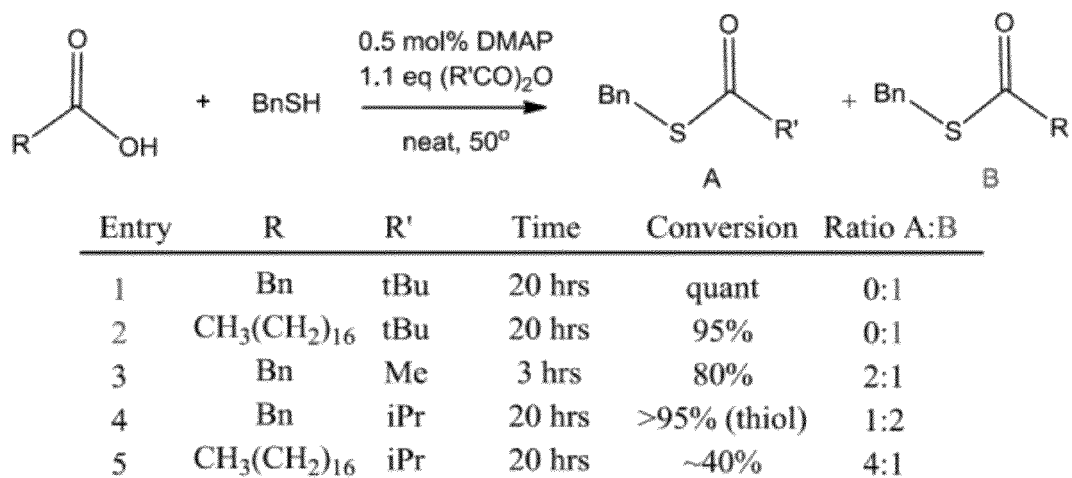
FIG. 11 shows results from experiments performed.

Activation of Carboxylic Acids with Pivalic Anhydride for Nucleophilic Addition of $R_3SiSH$ Under Solvent-Free Conditions Thiols undergo selective thioesterification with carboxylic acids via activation by catalytic DMAP and 1.1 equiv. $(tBuCO)_2O$ under mild, solvent-free conditions (FIG. 11). Utilization of solid-supported DMAP and a hydrolytically stable $R_3SiSH$ (such as $Ph_3SiSH$, TIPSSH, or $HS-Si(OtBu)_3$) will lead to a conditionally mild (though acidic) activation of RCOOH (to produce thioester and thus, thionoester) for subsequent addition of a nucleophile in a solvent-free, atom-economical reaction. $(tBuO)_3SiSH$ is hydrolytically stable to serve as a coupling partner to form $RC(=S)OSi(OtBu)_3$.

The invention claimed is:
1. A compound comprising the following formula:

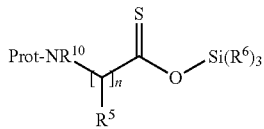

wherein,
Prot is a protecting group, wherein Prot is tert-butoxycarbonyl (Boc) or fluorenylmethyloxycarbonyl (Fmoc), peptide, or linker to a substrate or biological material, or $R^{13}$;
n is 1, 2, 3, 4, 5, or 6;
each $R^5$ is independently selected from hydrogen, alkyl, hydroxyalkyl, thiolalkyl, aminoalkyl, selenoalkyl, carboxylalkyl, aryl, or heterocyclyl, wherein $R^5$ is optionally substituted with one or more $R^{11}$;
each $R^6$ is independently selected from hydrogen, alkyl, aryl, and heterocyclyl, wherein $R^6$ is optionally substituted by one or more substituents independently selected from halogen, alkyl, and alkoxy;
$R^{10}$ is hydrogen, alkyl, or acyl, or
$R^{10}$ and Prot and the attached atoms form a protecting group comprising a 4 to 7 member heterocyclic ring, wherein the heterocyclyl is optionally substituted with one or more $R^{11}$ or
or $R^{10}$ and $R^5$ and the atoms to which they are attached to form a 4-7 membered heterocyclic ring optionally substituted with one or more $R^{11}$;
$R^{11}$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{11}$ is optionally substituted with $R^{12}$;
$R^{12}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;
$R^{13}$ is alkyl, alkanoyl, formyl, alkylcarboxy, alkylcarbamoyl wherein $R^{13}$ is optionally substituted with $R^{14}$
$R^{14}$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{14}$ is optionally substituted with $R^{15}$;
$R^{15}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

2. The composition of claim 1, wherein n is 1 or 2.

3. The composition of claim 1, where the biological material is a polypeptide, enzyme, receptor, nucleic acid, cell, antibody, saccharide, or glycopeptide.

4. The composition of claim 1, wherein the linker is an peptide, a nucleic acid, hydrocarbon, polyethylene glycol, polysaccharide, acrylate polymer, or other polymer.

5. A compound selected from N-alpha-Boc-alanine-O-trimethylsilylthionoester,
N-beta-Boc-beta-alanine-O-trimethylsilylthionoester,
N-alpha-Boc-N-alpha-methyl-alanine-O-trimethylsilylthionoester,
N-alpha-Boc-alpha-aminobutyric acid O-trimethylsilylthionoester,
N-Boc-4-aminobutanoic acid O-trimethylsilylthionoester,
N-alpha-Boc-alpha-aminoisobutyric acid O-trimethylsilylthionoester,
N-alpha-Boc-$N^G$-(4-Methoxy-2,3,6 trimethylbenzenesulfonyl)-arginine-O-trimethylsilylthionoester,
N-alpha-Boc-$N^G$-nitro-arginine-O-trimethylsilylthionoester,
N-alpha-Boc-$N^G$-tosyl-arginine-O-trimethylsilylthionoester,
N-alpha-Boc-$N^G$,$N^G$-bis-CBZ-arginine-O-trimethylsilylthionoester,
N-alpha-Boc-asparagine-O-trimethylsilylthionoester,
N-alpha-Boc-asparagine-O-trimethylsilylthionoester,
N-alpha-Boc-beta-trityl-asparagine-O-trimethylsilylthionoester,
N-alpha-Boc-N-beta-xanthyl-asparagine-O-trimethylsilylthionoester,
N-alpha-Boc-isoasparagine-O-trimethylsilylthionoester,
N-alpha-Boc-aspartic acid alpha-O-trimethylsilylthionoester beta-1-adamantyl ester,
N-alpha-Boc-aspartic acid alpha-O-trimethylsilylthionoester beta-2-adamantyl ester,
N-alpha-Boc-aspartic acid alpha-benzyl ester beta-O-trimethylsilylthionoester,
N-alpha-Boc-N-alpha-methyl-valine-O-trimethylsilylthionoester,
N-alpha-Boc-valine-O-trimethylsilylthionoester,
Boc-6-aminohexanoic acid O-trimethylsilylthionoester,
N-alpha-Boc-tert-leucine-O-trimethylsilylthionoester,
N-alpha-Boc-S-acetamidomethyl-cysteine-O-trimethylsilylthionoester,
N-alpha-Boc-S-benzyl-cysteine-O-trimethylsilylthionoester,
N-alpha-Boc-S-p-methylbenzyl-cysteine-O-trimethylsilylthionoester,
N-alpha-Boc-S-p-methoxybenzyl-cysteine-O-trimethylsilylthionoester,
N-alpha-Boc-S-trityl-cysteine-O-trimethylsilylthionoester,
N-alpha-Boc-beta-cyclohexyl-alanine-O-trimethylsilylthionoester,
N-alpha-Boc-glutamic acid gama-O-trimethylsilylthionoester alpha-benzyl ester,
N-alpha-Boc-glutamic acid gama-benzyl ester alpha-O-trimethylsilylthionoester,
N-alpha-Boc-glutamic acid gama-cyclohexyl ester alpha-O-trimethylsilylthionoester, N-alpha-Boc-glutamic acid gama-tert-butyl ester alpha-O-trimethylsilylthionoester,
N-alpha-Boc-gama-trityl-glutamine-O-trimethylsilylthionoester,
N-alpha-Boc-gama-xanthyl-glutamine-O-trimethylsilylthionoester,
N-alpha-N-im-di-Boc-histidine-O-trimethylsilylthionoester,
N-alpha-Boc-N-im-tosyl-histidine-O-trimethylsilylthionoester,
N-alpha-Boc-N-im-dinitrophenyl-histidine-O-trimethylsilylthionoester,
N-alpha-Boc-N-im-trityl-histidine-O-trimethylsilylthionoester,
N-alpha-Boc-trans-4-hydroxyproline-O-trimethylsilylthionoester,
N-alpha-Boc-glycine-O-trimethylsilylthionoester,
N-alpha-Boc-isoleucine-O-trimethylsilylthionoester,
N-alpha-Boc-N-epsilon-acetyl-lysine-O-trimethylsilylthionoester,
N-alpha,epsilon-di-Boc-lysine-O-trimethylsilylthionoester,
N-alpha-Boc-N-epsilon-2-chloro-CBZ-lysine-O-trimethylsilylthionoester,
N-alpha-Boc-N-epsilon-trifluoroacetyl-lysine-O-trimethylsilylthionoester,
N-alpha-Boc-leucine-O-trimethylsilylthionoester,
N-alpha-Boc-methionine-sulfone-O-trimethylsilylthionoester,
N-alpha-Boc-methionine-O-trimethylsilylthionoester,
N-alpha-Boc-methionine-sulfoxide-O-trimethylsilylthionoester,
N-alpha-Boc-N-alpha-methyl-norleucine-O-trimethylsilylthionoester,
N-alpha-Boc-norleucine-O-trimethylsilylthionoester,
N-alpha-Boc-norvaline-O-trimethylsilylthionoester,
N-alpha-Boc-3,4-dehydro-proline-O-trimethylsilylthionoester,
N-alpha-Boc-proline-O-trimethylsilylthionoester,
N-alpha-Boc-N-alpha-methyl-phenylalanine-O-trimethylsilylthionoester,
N-alpha-Boc-4-chloro-phenylalanine-O-trimethylsilylthionoester,
N-alpha-Boc-phenylalanine-O-trimethylsilylthionoester,
N-alpha-Boc-phenylglycine-O-trimethylsilylthionoester,
N-alpha-Boc-N-δ-benzyloxycarbonyl-ornithine-O-trimethylsilylthionoester,
N-alpha-Boc-sarcosine-O-trimethylsilylthionoester,
N-alpha-Boc-O-benzyl-serine-O-trimethylsilylthionoester,
N-alpha-Boc-O-methyl-serine-O-trimethylsilylthionoester,
N-alpha-Boc-O-tert-butyl-serine-O-trimethylsilylthionoester,
N-1-Boc-1,2,3,4,-tetrahydro-isoquinoline-3-carboxylic acid alpha-O-trimethylsilylthionoester,
N-alpha-Boc-N-in-Boc-trypophan-O-trimethylsilylthionoester,
N-alpha-Boc-N-in-formyl-tryptophan-O-trimethylsilylthionoester,
N-alpha-Boc-N-in-mesitylene-2-sulfonyl-tryptophan-O-trimethylsilylthionoester,
N-alpha-Boc-tyrosine-O-trimethylsilylthionoester,
N-alpha-Boc-N-alpha-methyl-O-benzyl-tyrosine-O-trimethylsilylthionoester,
N-alpha-Boc-O-2-bromobenzyloxycarbonyl-tyrosine-O-trimethylsilylthionoester,
N-alpha-Boc-O-benzyl-tyrosine-O-trimethylsilylthionoester,
N-alpha-Boc-O-2,6-dichlorobenzyl-tyrosine-O-trimethylsilylthionoester,
N-alpha-Boc-O-ethyl-tyrosine-O-trimethylsilylthionoester,
N-alpha-Boc-O-methyl-tyrosine-O-trimethylsilylthionoester,
N-alpha-Boc-O-tert-butyl-tyrosine-O-trimethylsilylthionoester,
N-alpha-Boc-O-benzyl-threonine-O-trimethylsilylthionoester,
N-alpha-Boc-threonine-O-trimethylsilylthionoester,
N-alpha-Fmoc-alanine-O-trimethylsilylthionoester,
N-beta-Fmoc-beta-alanine-O-trimethylsilylthionoester,
N-alpha-Fmoc-N-alpha-methyl-alanine-O-trimethylsilylthionoester,
N-alpha-Fmoc-alpha-aminobutyric acid O-trimethylsilylthionoester,
N-Fmoc-4-aminobutanoic acid O-trimethylsilylthionoester,
N-alpha-Fmoc-alpha-aminoisobutyric acid O-trimethylsilylthionoester,
N-alpha-Fmoc-$N^G$-(4-Methoxy-2,3,6 trimethylbenzenesulfonyl)-arginine-O-trimethylsilylthionoester,
N-alpha-Fmoc-$N^G$-nitro-arginine-O-trimethylsilylthionoester,
N-alpha-Fmoc-$N^G$-tosyl-arginine-O-trimethylsilylthionoester,
N-alpha-Fmoc-$N^G,N^G$-bis-CBZ-arginine-O-trimethylsilylthionoester,
N-alpha-Fmoc-asparagine-O-trimethylsilylthionoester,
N-alpha-Fmoc-asparagine-O-trimethylsilylthionoester,
N-alpha-Fmoc-beta-trityl-asparagine-O-trimethylsilylthionoester,
N-alpha-Fmoc-N-beta-xanthyl-asparagine-O-trimethylsilylthionoester,
N-alpha-Fmoc-isoasparagine-O-trimethylsilylthionoester,
N-alpha-Fmoc-aspartic acid alpha-O-trimethylsilylthionoester beta-1-adamantyl ester,
N-alpha-Fmoc-aspartic acid alpha-O-trimethylsilylthionoester beta-2-adamantyl ester,
N-alpha-Fmoc-aspartic acid alpha-benzyl ester beta-O-trimethylsilylthionoester,
N-alpha-Fmoc-N-alpha-methyl-valine-O-trimethylsilylthionoester,
N-alpha-Fmoc-valine-O-trimethylsilylthionoester,
Fmoc-6-aminohexanoic acid 0-trimethylsilylthionoester,
N-alpha-Fmoc-tert-leucine-O-trimethylsilylthionoester,
N-alpha-Fmoc-S-acetamidomethyl-cysteine-O-trimethylsilylthionoester,
N-alpha-Fmoc-S-benzyl-cysteine-O-trimethylsilylthionoester,
N-alpha-Fmoc-S-p-methylbenzyl-cysteine-O-trimethylsilylthionoester,
N-alpha-Fmoc-S-p-methoxybenzyl-cysteine-O-trimethylsilylthionoester,
N-alpha-Fmoc-S-trityl-cysteine-O-trimethylsilylthionoester,
N-alpha-Fmoc-beta-cyclohexyl-alanine-O-trimethylsilylthionoester,
N-alpha-Fmoc-glutamic acid gama-O-trimethylsilylthionoester alpha-benzyl ester,
N-alpha-Fmoc-glutamic acid gama-benzyl ester alpha-O-trimethylsilylthionoester, N-alpha-Fmoc-glutamic acid gama-cyclohexyl ester alpha-O-trimethylsilylthionoester,
N-alpha-Fmoc-glutamic acid gama-tert-butyl ester alpha-O-trimethylsilylthionoester,
N-alpha-Fmoc-gama-trityl-glutamine-O-trimethylsilylthionoester,
N-alpha-Fmoc-gama-xanthyl-glutamine-O-trimethylsilylthionoester,
N-alpha-N-im-di-Fmoc-histidine-O-trimethylsilylthionoester,
N-alpha-Fmoc-N-im-tosyl-histidine-O-trimethylsilylthionoester,
N-alpha-Fmoc-N-im-dinitrophenyl-histidine-O-trimethylsilylthionoester,
N-alpha-Fmoc-N-im-trityl-histidine-O-trimethylsilylthionoester,
N-alpha-Fmoc-trans-4-hydroxyproline-O-trimethylsilylthionoester,
N-alpha-Fmoc-glycine-O-trimethylsilylthionoester,
N-alpha-Fmoc-isoleucine-O-trimethylsilylthionoester,
N-alpha-Fmoc-N-epsilon-acetyl-lysine-O-trimethylsilylthionoester,
N-alpha,epsilon-di-Fmoc-lysine-O-trimethylsilylthionoester,
N-alpha-Fmoc-N-epsilon-2-chloro-CBZ-lysine-O-trimethylsilylthionoester,
N-alpha-Fmoc-N-epsilon-trifluoroacetyl-lysine-O-trimethylsilylthionoester,
N-alpha-Fmoc-leucine-O-trimethylsilylthionoester,
N-alpha-Fmoc-methionine-sulfone-O-trimethylsilylthionoester,
N-alpha-Fmoc-methionine-O-trimethylsilylthionoester,
N-alpha-Fmoc-methionine-sulfoxide-O-trimethylsilylthionoester,
N-alpha-Fmoc-N-alpha-methyl-norleucine-O-trimethylsilylthionoester,
N-alpha-Fmoc-norleucine-O-trimethylsilylthionoester,
N-alpha-Fmoc-norvaline-O-trimethylsilylthionoester,
N-alpha-Fmoc-3,4-dehydro-proline-O-trimethylsilylthionoester,
N-alpha-Fmoc-proline-O-trimethylsilylthionoester,
N-alpha-Fmoc-N-alpha-methyl-phenylalanine-O-trimethylsilylthionoester,
N-alpha-Fmoc-4-chloro-phenylalanine-O-trimethylsilylthionoester,
N-alpha-Fmoc-phenylalanine-O-trimethylsilylthionoester,
N-alpha-Fmoc-phenylglycine-O-trimethylsilylthionoester,
N-alpha-Fmoc-N-δ-benzyloxycarbonyl-omithine-O-trimethylsilylthionoester,
N-alpha-Fmoc-sarcosine-O-trimethylsilylthionoester,
N-alpha-Fmoc-O-benzyl-serine-O-trimethylsilylthionoester,
N-alpha-Fmoc-O-methyl-serine-O-trimethylsilylthionoester,
N-alpha-Fmoc-O-tert-butyl-serine-O-trimethylsilylthionoester,
N-1-Fmoc-1,2,3,4,-tetrahydro-isoquinoline-3-carboxylic acid alpha-O-trimethylsilylthionoester,
N-alpha-Fmoc-N-in-Fmoc-trypophan-O-trimethylsilylthionoester,
N-alpha-Fmoc-N-in-formyl-tryptophan-O-trimethylsilylthionoester,
N-alpha-Fmoc-N-in-mesitylene-2-sulfonyl-tryptophan-O-trimethylsilylthionoester,
N-alpha-Fmoc-tyrosine-O-trimethylsilylthionoester,
N-alpha-Fmoc-N-alpha-methyl-O-benzyl-tyrosine-O-trimethylsilylthionoester,
N-alpha-Fmoc-O-2-bromobenzyloxycarbonyl-tyrosine-O-trimethylsilylthionoester,
N-alpha-Fmoc-O-benzyl-tyrosine-O-trimethylsilylthionoester,
N-alpha-Fmoc-O-2,6-dichlorobenzyl-tyrosine-O-trimethylsilylthionoester,
N-alpha-Fmoc-O-ethyl-tyrosine-O-trimethylsilylthionoester,
N-alpha-Fmoc-O-methyl-tyrosine-O-trimethylsilylthionoester,
N-alpha-Fmoc-O-tert-butyl-tyrosine-O-trimethylsilylthionoester,
N-alpha-Fmoc-O-benzyl-threonine-O-trimethylsilylthionoester, and
N-alpha-Fmoc-threonine-O-trimethylsilylthionoester.

6. A compound comprising the following formula:

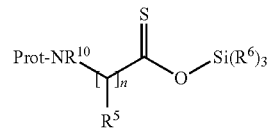

wherein,
Prot is a protecting group, wherein Prot is 4-methoxy-2,3,6-trimethylphenyl)sulfonyl (Mtr), 2,2,5,7,8-pentamethyl-chroman-6-sulphonyl (Pmc), tosyl (Tos), mesitylenesulfonyl (Mts), 4,4'-dimethoxybenzhydryl (Mbh), 2,4,6-trimethoxybenzyl (Tmob), tripheylmethyl (Trt), tert-buty (tBu), benzyl (Bzl), t-Butoxymethyl ether (Bum), (2,4-dinitrophenol) Dnp, benzyloxymethyl (Bom), benzyloxycarbonyl (Z), 2-chloro-benzyloxycarbonyl (CIZ), formyl (CHO) or 2-bromobenzyloxycarbonyl (BrZ);
n is 1, 2, 3, 4, 5, or 6;
each $R^5$ is independently selected from hydrogen, alkyl, hydroxyalkyl, thiolalkyl, aminoalkyl, selenoalkyl, carboxylalkyl, aryl, or heterocyclyl, wherein $R^5$ is optionally substituted with one or more $R^{11}$;
each $R^6$ is independently selected from hydrogen, alkyl, aryl, and heterocyclyl, wherein $R^6$ is optionally substituted by one or more substituents independently selected from halogen, alkyl, and alkoxy;
$R^{10}$ is hydrogen, alkyl, or acyl, or
$R^{10}$ and Prot and the attached atoms form a protecting group comprising a 4 to 7 member heterocyclic ring, wherein the heterocyclyl is optionally substituted with one or more $R^{11}$ or
or $R^{10}$ and $R^5$ and the atoms to which they are attached to form a 4-7 membered heterocyclic ring optionally substituted with one or more $R^{11}$;
$R^{11}$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{11}$ is optionally substituted with $R^{12}$;
$R^{12}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^{13}$ is alkyl, alkanoyl, formyl, alkylcarboxy, alkylcarbamoyl wherein $R^{13}$ is optionally substituted with $R^{14}$ $R^{14}$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{14}$ is optionally substituted with $R^{15}$;

$R^{15}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

7. A compound comprising the following formula:

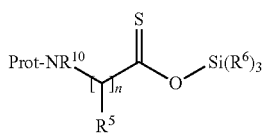

wherein,

Prot is a protecting group, peptide, or linker to a substrate or biological material, or $R^{13}$;

n is 1, 2, 3, 4, 5, or 6;

each $R^5$ is independently selected from hydrogen, alkyl, hydroxyalkyl, thiolalkyl, aminoalkyl, selenoalkyl, carboxylalkyl, aryl, or heterocyclyl, wherein $R^5$ is optionally substituted with one or more $R^{11}$;

each $R^6$ is independently selected from hydrogen, alkyl, aryl, and heterocyclyl, wherein $R^6$ is optionally substituted by one or more substituents independently selected from halogen, alkyl, and alkoxy;

$R^{10}$ is hydrogen or $R^{10}$ and Prot and the attached atoms form a protecting group comprising a 4 to 7 member heterocyclic ring, wherein the heterocyclyl is optionally substituted with one or more $R^{11}$ or or $R^{10}$ and $R^5$ and the atoms to which they are attached to form a 4-7 membered heterocyclic ring optionally substituted with one or more $R^{11}$;

$R^{11}$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{11}$ is optionally substituted with $R^{12}$;

$R^{12}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^{13}$ is alkyl, alkanoyl, formyl, alkylcarboxy, alkylcarbamoyl wherein $R^{13}$ is optionally substituted with $R^{14}$ $R^{14}$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{14}$ is optionally substituted with $R^{15}$;

$R^{15}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

* * * * *